US008198257B2

United States Patent
Aubourg et al.

(10) Patent No.: US 8,198,257 B2
(45) Date of Patent: Jun. 12, 2012

(54) CYP46A1 GENE FOR THE TREATMENT OF ALZHEIMER'S DISEASE

(75) Inventors: Patrick Aubourg, Paris (FR); Nathalie Cartier-Lacave, Paris (FR); Eloise Hudry, Paris (FR)

(73) Assignee: Institut National de la Sante et de la Recherche Medicale (INSERM) (FR)

( * ) Notice: Subject to any disclaimer, the term of this patent is extended or adjusted under 35 U.S.C. 154(b) by 0 days.

(21) Appl. No.: 12/678,020

(22) PCT Filed: Sep. 11, 2008

(86) PCT No.: PCT/EP2008/062047
§ 371 (c)(1),
(2), (4) Date: Oct. 26, 2010

(87) PCT Pub. No.: WO2009/034127
PCT Pub. Date: Mar. 19, 2009

(65) Prior Publication Data
US 2011/0034540 A1 Feb. 10, 2011

Related U.S. Application Data

(60) Provisional application No. 60/971,624, filed on Sep. 12, 2007.

(51) Int. Cl.
*A61K 48/00* (2006.01)
(52) U.S. Cl. .................................. 514/44 R; 435/320.1
(58) Field of Classification Search .......................... None
See application file for complete search history.

(56) References Cited

U.S. PATENT DOCUMENTS

2002/0141980 A1* 10/2002 Bankiewicz et al. ...... 424/93.21

FOREIGN PATENT DOCUMENTS

| WO | 03/046579 | 6/2003 |
| WO | 03/048384 | 6/2003 |
| WO | 2004/055201 | 7/2004 |

OTHER PUBLICATIONS

Mast et al. Broad Substrate Specificity of Human Cytochrome P450 46A1 Which Initiates Cholesterol Degradation in the Brain† Biochemistry, 2003, vol. 42, pp. 14284-14292.*
del Pozo et al. Polymorphism in the Cholesterol 24S-Hydroxylase Gene (CYP46A1) Associated with the APOE3 Allele Increases the Risk of Alzheimer's Disease and of Mild Cognitive Impairment Progressing to Alzheimer's Disease Dementia Geriatric Congnative Diorders, 2006, vol. 21, pp. 81-87.*
Auricchio et al. Pseudotyped AAV vectors for constitutive and regulated gene expression in the eye Vision Research, 2003, vol. 43, pp. 913-918.*
Feng et al. Adeno-Associated Viral Vector-Mediated APOE Expression in Alzheimer'S Disease Mice: Low CNS Immune Response, Long-Term Expression, and Astrocyte Specificity Frontiers in Bioscience, 2004, vol. 9, pp. 1540-1546.*
Aebischer et al. Recombinant proteins for neurodegenerative diseases: the delivery issue Trends in Neuroscience, 2001, vol. 24, pp. 533-540.*
Lund et al., cDNA Cloning of Cholesterol 24-Hydroxylase, a Mediator of Cholesterol Homeostasis in the Brain, Proc. Natl. Acad. Sci. USA, Jun. 1999, pp. 7238-7243, vol. 96.

* cited by examiner

*Primary Examiner* — Deborah Crouch
(74) *Attorney, Agent, or Firm* — Thompson Coburn LLP

(57) ABSTRACT

The invention relates to a viral vector for treating Alzheimers disease, which vector comprises a cholesterol 24-hydroxylase (CYP46A1) encoding nucleic acid. In a preferred embodiment, the viral vector may be an Adeno-Associated-Virus (AAV) vector, preferably an AVV5 vector. The vector may be useful for the manufacture of a pharmaceutical composition for the treatment of Alzheimers disease in a subject, wherein the vector is to be administered directly into the brain of the subject or by intravenous or intrathecal injection.

13 Claims, 12 Drawing Sheets

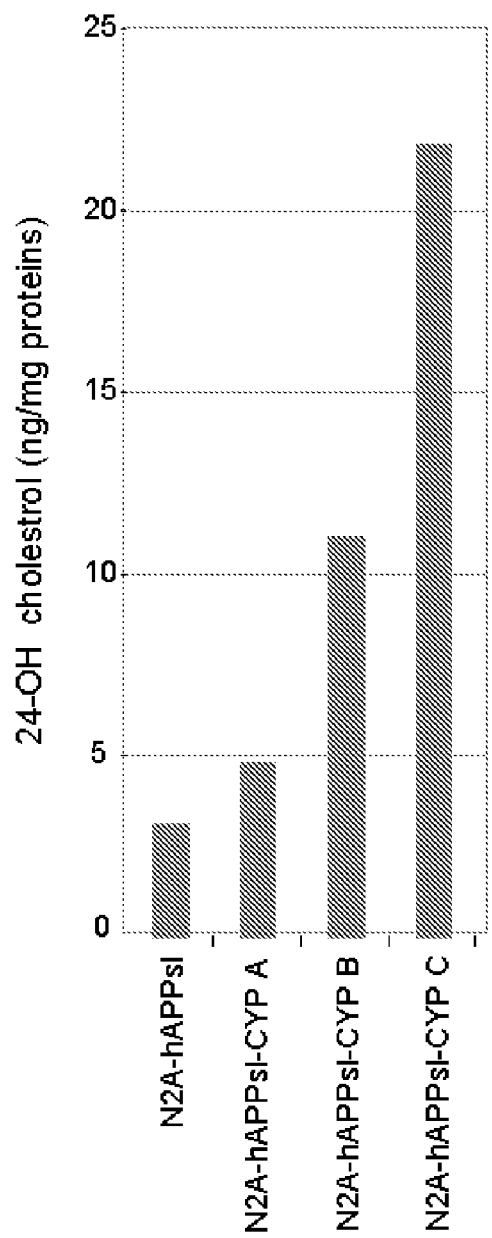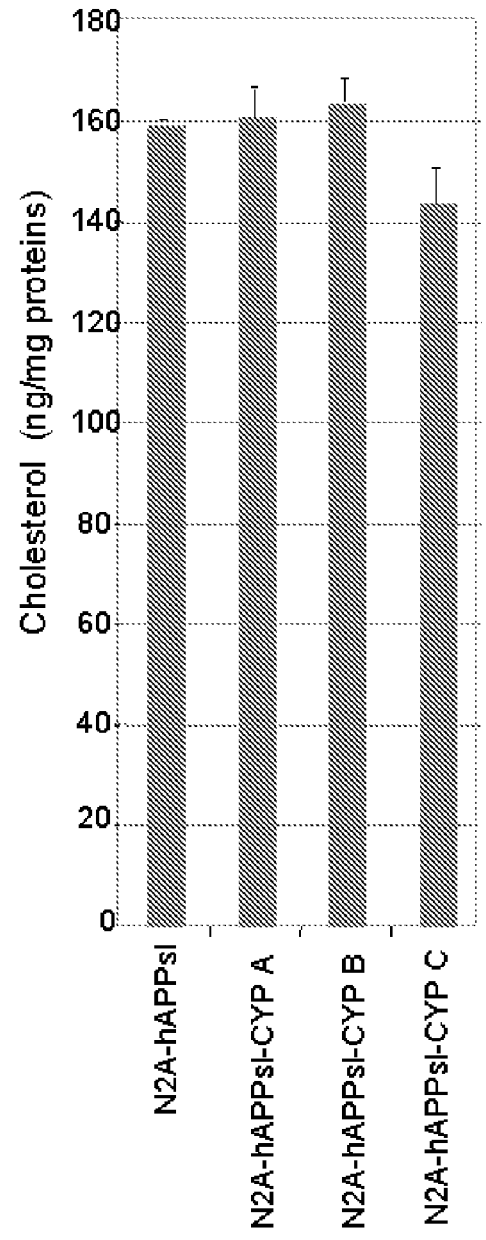
FIGURE 2C
FIGURE 2D

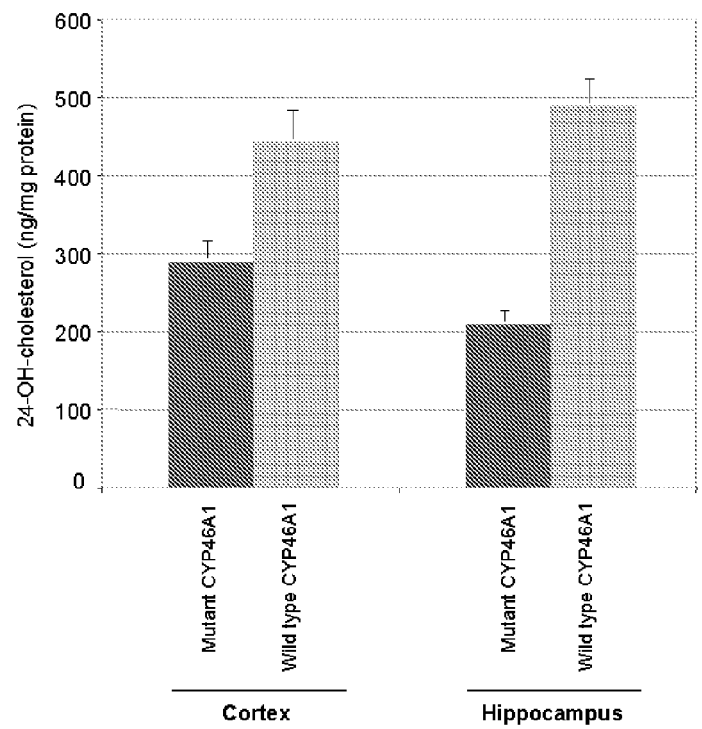
FIGURE 3
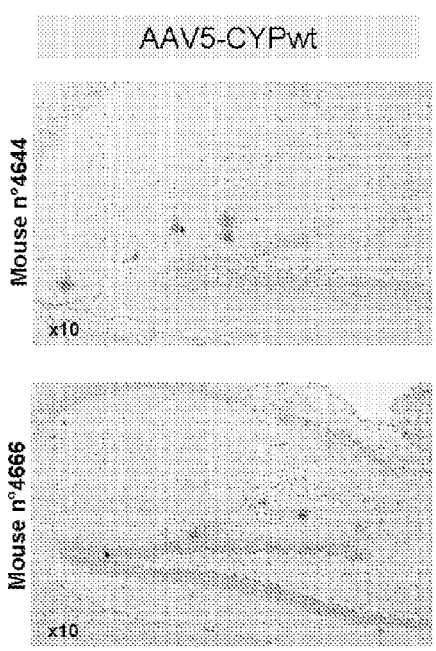
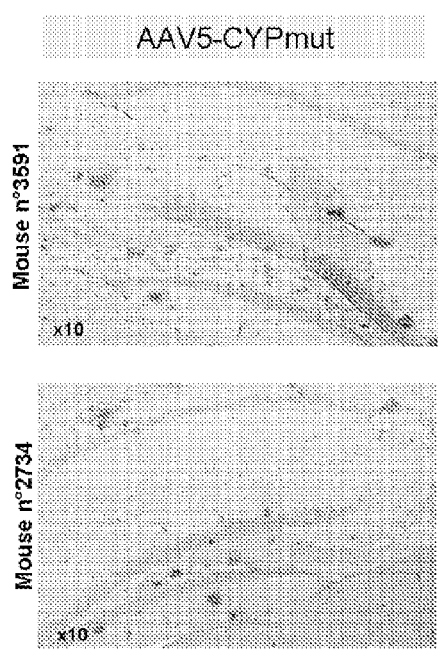
FIGURE 4A          FIGURE 4B

A: CYPwt injected APP mice
B: control injected APP mice

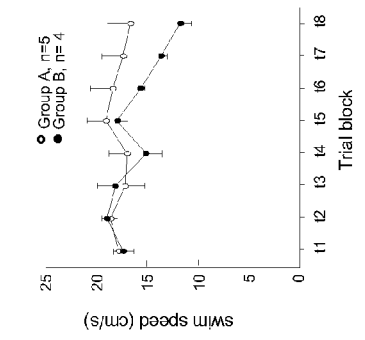

A: Acquisition phase

Path length 2-way RM-ANOVA
Treatment effect: p=0.054
Trial block effect: p<0.001
Treatment x trial block interaction effect: p=0.583

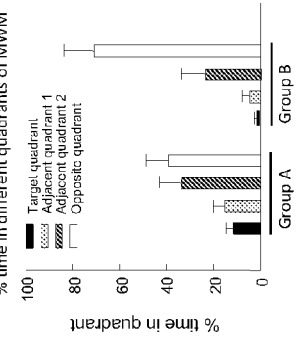

B: Swim speed

2-way RM-ANOVA
Treatment effect: p=0.401
Trial block effect: p<0.001
Treatment x trial block interaction effect: p=0.059

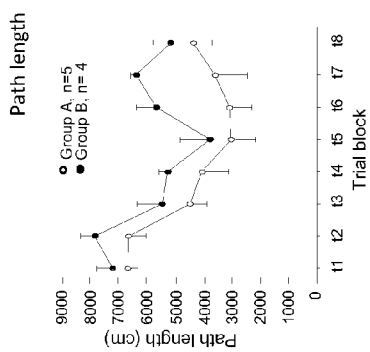

Escape Latency 2-way RM-ANOVA
Treatment effect: p=0.091
Trial block effect: p<0.001
Treatment x trial block interaction effect: p=0.098

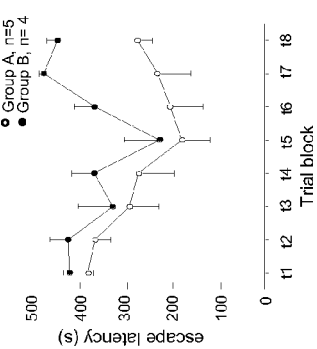

C: Probe trial:

% time in different quadrants of MWM

|  | Group A | Group B |
|---|---|---|
| Entries target | 1.4 +/- 0.4 | 0 +/- 0 | P=0.018 |
| Path length (cm) | 1703 +/- 285 | 1244 +/- 148 | P= 0.229 |

Figure 5

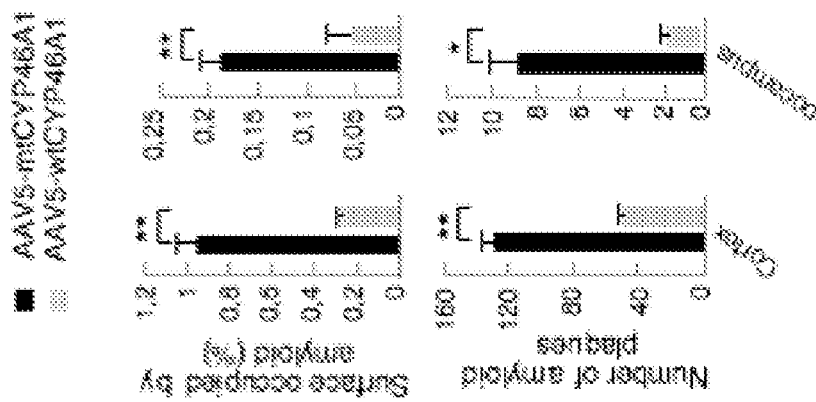
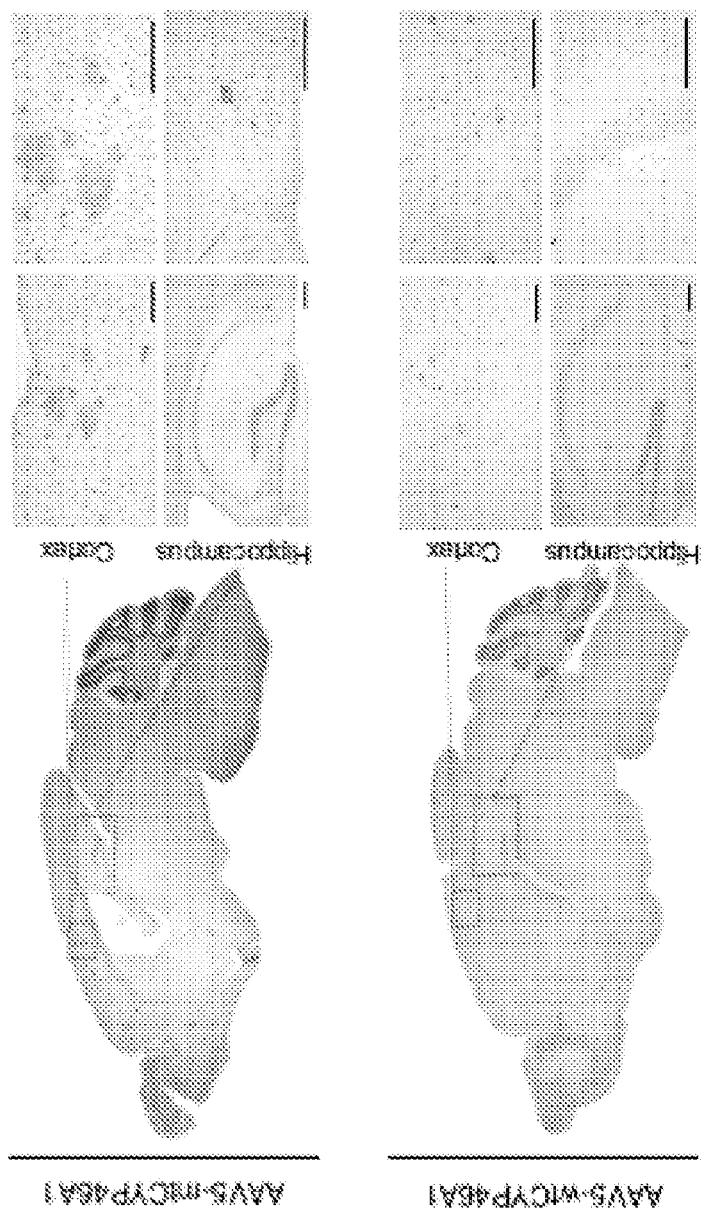
Figure 7A
Figure 7B

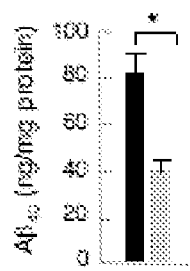
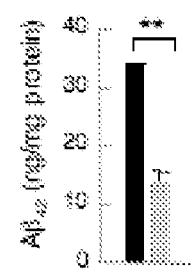
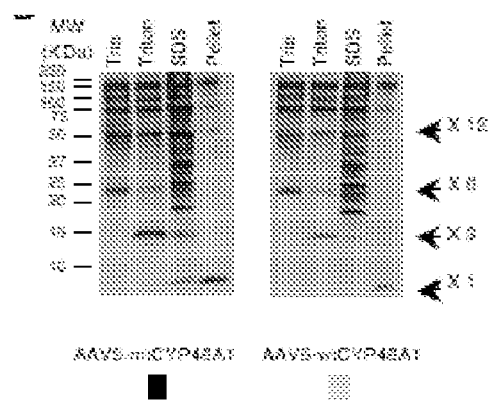
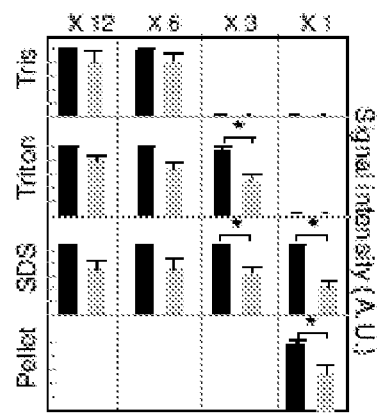
Figure 7C
Figure 7D

SEQUENCE LISTING

<160> NUMBER OF SEQ ID NOS: 32

<210> SEQ ID NO 1
<211> LENGTH: 2138
<212> TYPE: DNA
<213> ORGANISM: Homo sapiens
<220> FEATURE:
<221> NAME/KEY: CDS
<222> LOCATION: (1)..(1503)

<400> SEQUENCE: 1

| | | | | | | | | | | | | | | | | |
|---|---|---|---|---|---|---|---|---|---|---|---|---|---|---|---|---|
| atg | agc | ccc | ggg | ctg | ctg | ctg | ctc | ggc | agc | gcc | gtc | ctg | ctc | gcc | ttc | 48 |
| Met | Ser | Pro | Gly | Leu | Leu | Leu | Leu | Gly | Ser | Ala | Val | Leu | Leu | Ala | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | ctc | tgc | tgc | acc | ttc | gtg | cac | cgc | gct | cgc | agc | cgc | tac | gag | cac | 96 |
| Gly | Leu | Cys | Cys | Thr | Phe | Val | His | Arg | Ala | Arg | Ser | Arg | Tyr | Glu | His | |
| | | 20 | | | | | 25 | | | | | 30 | | | | |

| | | | | | | | | | | | | | | | | |
|---|---|---|---|---|---|---|---|---|---|---|---|---|---|---|---|---|
| atc | ccc | ggg | ccg | ccg | cgg | ccc | agt | ttc | ctt | cta | gga | cac | ctc | ccc | tgc | 144 |
| Ile | Pro | Gly | Pro | Pro | Arg | Pro | Ser | Phe | Leu | Leu | Gly | His | Leu | Pro | Cys | |
| | | | 35 | | | | | 40 | | | | | 45 | | | |

| | | | | | | | | | | | | | | | | |
|---|---|---|---|---|---|---|---|---|---|---|---|---|---|---|---|---|
| ttt | tgg | aaa | aag | gat | gag | gtt | ggt | ggc | cgt | gtg | ctc | caa | gat | gtg | ttt | 192 |
| Phe | Trp | Lys | Lys | Asp | Glu | Val | Gly | Gly | Arg | Val | Leu | Gln | Asp | Val | Phe | |
| 50 | | | | | 55 | | | | | 60 | | | | | | |

| | | | | | | | | | | | | | | | | |
|---|---|---|---|---|---|---|---|---|---|---|---|---|---|---|---|---|
| ttg | gat | tgg | gct | aag | aag | tat | gga | cct | gtt | gtg | cgg | gtc | aac | gtc | ttc | 240 |
| Leu | Asp | Trp | Ala | Lys | Lys | Tyr | Gly | Pro | Val | Val | Arg | Val | Asn | Val | Phe | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cac | aaa | acc | tca | gtc | atc | gtc | acg | agt | cct | gag | tcg | gtt | aag | aag | ttc | 288 |
| His | Lys | Thr | Ser | Val | Ile | Val | Thr | Ser | Pro | Glu | Ser | Val | Lys | Lys | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| ctg | atg | tca | acc | aag | tac | aac | aag | gac | tcc | aag | atg | tac | cgt | gcg | ctc | 336 |
| Leu | Met | Ser | Thr | Lys | Tyr | Asn | Lys | Asp | Ser | Lys | Met | Tyr | Arg | Ala | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | act | gtg | ttt | ggt | gag | aga | ctc | ttc | ggc | caa | ggc | ttg | gtg | tcc | gaa | 384 |
| Gln | Thr | Val | Phe | Gly | Glu | Arg | Leu | Phe | Gly | Gln | Gly | Leu | Val | Ser | Glu | |
| | | | 115 | | | | | 120 | | | | | 125 | | | |

| | | | | | | | | | | | | | | | | |
|---|---|---|---|---|---|---|---|---|---|---|---|---|---|---|---|---|
| tgc | aac | tat | gag | cgc | tgg | cac | aag | cag | cgg | aga | gtc | ata | gac | ctg | gcc | 432 |
| Cys | Asn | Tyr | Glu | Arg | Trp | His | Lys | Gln | Arg | Arg | Val | Ile | Asp | Leu | Ala | |
| | | 130 | | | | | 135 | | | | | 140 | | | | |

| | | | | | | | | | | | | | | | | |
|---|---|---|---|---|---|---|---|---|---|---|---|---|---|---|---|---|
| ttc | agc | cgg | agc | tcc | ttg | gtt | agc | tta | atg | gaa | aca | ttc | aac | gag | aag | 480 |
| Phe | Ser | Arg | Ser | Ser | Leu | Val | Ser | Leu | Met | Glu | Thr | Phe | Asn | Glu | Lys | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| gct | gag | cag | ctg | gtg | gag | att | cta | gaa | gcc | aag | gca | gat | ggg | cag | acc | 528 |
| Ala | Glu | Gln | Leu | Val | Glu | Ile | Leu | Glu | Ala | Lys | Ala | Asp | Gly | Gln | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| cca | gtg | tcc | atg | cag | gac | atg | ctg | acc | tac | acc | gcc | atg | gac | atc | ctg | 576 |
| Pro | Val | Ser | Met | Gln | Asp | Met | Leu | Thr | Tyr | Thr | Ala | Met | Asp | Ile | Leu | |
| | | | 180 | | | | | 185 | | | | | 190 | | | |

| | | | | | | | | | | | | | | | | |
|---|---|---|---|---|---|---|---|---|---|---|---|---|---|---|---|---|
| gcc | aag | gca | gct | ttt | ggg | atg | gag | acc | agt | atg | ctg | ctg | ggt | gcc | cag | 624 |
| Ala | Lys | Ala | Ala | Phe | Gly | Met | Glu | Thr | Ser | Met | Leu | Leu | Gly | Ala | Gln | |
| | | | 195 | | | | | 200 | | | | | 205 | | | |

| | | | | | | | | | | | | | | | | |
|---|---|---|---|---|---|---|---|---|---|---|---|---|---|---|---|---|
| aag | cct | ctg | tcc | cag | gca | gtg | aaa | ctt | atg | ttg | gag | gga | atc | act | gcg | 672 |
| Lys | Pro | Leu | Ser | Gln | Ala | Val | Lys | Leu | Met | Leu | Glu | Gly | Ile | Thr | Ala | |
| | | 210 | | | | | 215 | | | | | 220 | | | | |

| | | | | | | | | | | | | | | | | |
|---|---|---|---|---|---|---|---|---|---|---|---|---|---|---|---|---|
| tcc | cgc | aac | act | ctg | gca | aag | ttc | ctg | cca | ggg | aag | agg | aag | cag | ctc | 720 |
| Ser | Arg | Asn | Thr | Leu | Ala | Lys | Phe | Leu | Pro | Gly | Lys | Arg | Lys | Gln | Leu | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| cgg | gag | gtc | cgg | gag | agc | att | cgc | ttc | ctg | cgc | cag | gtg | ggc | agg | gac | 768 |
| Arg | Glu | Val | Arg | Glu | Ser | Ile | Arg | Phe | Leu | Arg | Gln | Val | Gly | Arg | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| tgg | gtc | cag | cgc | cgc | cgg | gaa | gcc | ctg | aag | agg | ggc | gag | gag | gtt | cct | 816 |

```
                    -continued

Trp Val Gln Arg Arg Glu Ala Leu Lys Arg Gly Glu Glu Val Pro
            260                 265                 270 gcc gac atc ctc aca cag att ctg aaa gct gaa gag gga gcc cag gac      864
Ala Asp Ile Leu Thr Gln Ile Leu Lys Ala Glu Glu Gly Ala Gln Asp
        275                 280                 285 gac gag ggt ctg ctg gac aac ttc gtc acc ttc ttc att gct ggt cac      912
Asp Glu Gly Leu Leu Asp Asn Phe Val Thr Phe Phe Ile Ala Gly His
    290                 295                 300 gag acc tct gcc aac cac ttg gcg ttc aca gtg atg gag ctg tct cgc      960
Glu Thr Ser Ala Asn His Leu Ala Phe Thr Val Met Glu Leu Ser Arg
305                 310                 315                 320 cag cca gag atc gtg gca agg ctg cag gcc gag gtg gat gag gtc att      1008
Gln Pro Glu Ile Val Ala Arg Leu Gln Ala Glu Val Asp Glu Val Ile
                325                 330                 335 ggt tct aag agg tac ctg gat ttc gag gac ctg ggg aga ctg cag tac      1056
Gly Ser Lys Arg Tyr Leu Asp Phe Glu Asp Leu Gly Arg Leu Gln Tyr
            340                 345                 350 ctg tcc cag gtc ctc aaa gag tcg ctg agg ctg tac cca cca gca tgg      1104
Leu Ser Gln Val Leu Lys Glu Ser Leu Arg Leu Tyr Pro Pro Ala Trp
        355                 360                 365 ggc acc ttt cgc ctg ctg gaa gag gag acc ttg att gat ggg gtc aga      1152
Gly Thr Phe Arg Leu Leu Glu Glu Glu Thr Leu Ile Asp Gly Val Arg
    370                 375                 380 gtc ccc ggc aac acc ccg ctc ttg ttc agc acc tat gtc atg ggg cgg      1200
Val Pro Gly Asn Thr Pro Leu Leu Phe Ser Thr Tyr Val Met Gly Arg
385                 390                 395                 400 atg gac aca tac ttt gag gac ccg ctg act ttc aac ccc gat cgc ttc      1248
Met Asp Thr Tyr Phe Glu Asp Pro Leu Thr Phe Asn Pro Asp Arg Phe
                405                 410                 415 ggc cct gga gca ccc aag cca cgg ttc acc tac ttc ccc ttc tcc ctg      1296
Gly Pro Gly Ala Pro Lys Pro Arg Phe Thr Tyr Phe Pro Phe Ser Leu
            420                 425                 430 ggc cac cgc tcc tgc atc ggg cag cag ttt gct cag atg gag gtg aag      1344
Gly His Arg Ser Cys Ile Gly Gln Gln Phe Ala Gln Met Glu Val Lys
        435                 440                 445 gtg gtc atg gca aag ctg ctg cag agg ctg gag ttc cgg ctg gtg ccc      1392
Val Val Met Ala Lys Leu Leu Gln Arg Leu Glu Phe Arg Leu Val Pro
    450                 455                 460 ggg cag cgc ttc ggg ctg cag gag cag gcc aca ctc aag cca ctg gac      1440
Gly Gln Arg Phe Gly Leu Gln Glu Gln Ala Thr Leu Lys Pro Leu Asp
465                 470                 475                 480 ccc gtg ctg tgc acc ctg cgg ccc cgc ggc tgg cag ccc gca ccc cca      1488
Pro Val Leu Cys Thr Leu Arg Pro Arg Gly Trp Gln Pro Ala Pro Pro
                485                 490                 495 cca ccc ccc tgc tga gggggcctcc aggcaggacg agactcctcg ggcaagggcc      1543
Pro Pro Pro Cys
            500 gtgcccgccc acctctgctg cccacggcca cccacccttc tccctgcc cgtccctgg       1603 gccaccttc acgctggctt ccagcgggcc ctctgccgac cgcctgcttc acacccctca    1663 gcgctccctg tcgcctgcgg actccatggc ccttcctgga ctggcccttg cccaactccc   1723 agccaccacc actgtcccta ccactgagcc cttgcacagg ccacttgctc agacgagaca   1783 ccctaactct tgctcactcc ctaaagccct cttcaggggt cacctcctcc aagaagccct   1843 ccttgccacc ccccgccggc aggggcccct cctctgtgct ccctcggtca cctgtgctac   1903 ctctaacacc acactgacca cactgtatcg tgagtgtccg ttgacgtgac caattgccct   1963 gccaggctgt cagcgcctca agggtagggt ctgcgtgtga tttgtctctg agcccctgt    2023 gcccacccag ggcccggcac agagtcgatg ctcaataaat gtgtgttgac tgcaaaaaaa   2083
```
aaaaaaaaaa aaaaaaaaaa aaaaaaaaaa aaaaaaaaaa aaaaaaaaaa aaaaa        2138

<210> SEQ ID NO 2
<211> LENGTH: 500
<212> TYPE: PRT
<213> ORGANISM: Homo sapiens

<400> SEQUENCE: 2

Met Ser Pro Gly Leu Leu Leu Gly Ser Ala Val Leu Leu Ala Phe
1               5                   10                  15

Gly Leu Cys Cys Thr Phe Val His Arg Ala Arg Ser Arg Tyr Glu His
            20                  25                  30

Ile Pro Gly Pro Pro Arg Pro Ser Phe Leu Leu Gly His Leu Pro Cys
            35                  40                  45

Phe Trp Lys Lys Asp Glu Val Gly Gly Arg Val Leu Gln Asp Val Phe
50                  55                  60

Leu Asp Trp Ala Lys Lys Tyr Gly Pro Val Val Arg Val Asn Val Phe
65                  70                  75                  80

His Lys Thr Ser Val Ile Val Thr Ser Pro Glu Ser Val Lys Lys Phe
                85                  90                  95

Leu Met Ser Thr Lys Tyr Asn Lys Asp Ser Lys Met Tyr Arg Ala Leu
            100                 105                 110

Gln Thr Val Phe Gly Glu Arg Leu Phe Gly Gln Gly Leu Val Ser Glu
            115                 120                 125

Cys Asn Tyr Glu Arg Trp His Lys Gln Arg Arg Val Ile Asp Leu Ala
            130                 135                 140

Phe Ser Arg Ser Ser Leu Val Ser Leu Met Glu Thr Phe Asn Glu Lys
145                 150                 155                 160

Ala Glu Gln Leu Val Glu Ile Leu Glu Ala Lys Ala Asp Gly Gln Thr
                165                 170                 175

Pro Val Ser Met Gln Asp Met Leu Thr Tyr Thr Ala Met Asp Ile Leu
            180                 185                 190

Ala Lys Ala Ala Phe Gly Met Glu Thr Ser Met Leu Leu Gly Ala Gln
            195                 200                 205

Lys Pro Leu Ser Gln Ala Val Lys Leu Met Leu Glu Gly Ile Thr Ala
210                 215                 220

Ser Arg Asn Thr Leu Ala Lys Phe Leu Pro Gly Lys Arg Lys Gln Leu
225                 230                 235                 240

Arg Glu Val Arg Glu Ser Ile Arg Phe Leu Arg Gln Val Gly Arg Asp
                245                 250                 255

Trp Val Gln Arg Arg Arg Glu Ala Leu Lys Arg Gly Glu Glu Val Pro
            260                 265                 270

Ala Asp Ile Leu Thr Gln Ile Leu Lys Ala Glu Gly Ala Gln Asp
            275                 280                 285

Asp Glu Gly Leu Leu Asp Asn Phe Val Thr Phe Ile Ala Gly His
            290                 295                 300

Glu Thr Ser Ala Asn His Leu Ala Phe Thr Val Met Glu Leu Ser Arg
305                 310                 315                 320

Gln Pro Glu Ile Val Ala Arg Leu Gln Ala Glu Val Asp Glu Val Ile
                325                 330                 335

Gly Ser Lys Arg Tyr Leu Asp Phe Glu Asp Leu Gly Arg Leu Gln Tyr
            340                 345                 350

Leu Ser Gln Val Leu Lys Glu Ser Leu Arg Leu Tyr Pro Pro Ala Trp
            355                 360                 365

```
Gly Thr Phe Arg Leu Leu Glu Glu Thr Leu Ile Asp Gly Val Arg
    370                 375                 380

Val Pro Gly Asn Thr Pro Leu Leu Phe Ser Thr Tyr Val Met Gly Arg
385                 390                 395                 400

Met Asp Thr Tyr Phe Glu Asp Pro Leu Thr Phe Asn Pro Asp Arg Phe
                405                 410                 415

Gly Pro Gly Ala Pro Lys Pro Arg Phe Thr Tyr Phe Pro Phe Ser Leu
            420                 425                 430

Gly His Arg Ser Cys Ile Gly Gln Gln Phe Ala Gln Met Glu Val Lys
        435                 440                 445

Val Val Met Ala Lys Leu Leu Gln Arg Leu Glu Phe Arg Leu Val Pro
    450                 455                 460

Gly Gln Arg Phe Gly Leu Gln Glu Gln Ala Thr Leu Lys Pro Leu Asp
465                 470                 475                 480

Pro Val Leu Cys Thr Leu Arg Pro Arg Gly Trp Gln Pro Ala Pro Pro
                485                 490                 495

Pro Pro Pro Cys
            500

<210> SEQ ID NO 3
<211> LENGTH: 21
<212> TYPE: DNA
<213> ORGANISM: artificial
<220> FEATURE:
<223> OTHER INFORMATION: primer

<400> SEQUENCE: 3
tgcacaggag ccaagagtga a                                          21

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
cacatcacag ctcccccacca                                           20

<210> SEQ ID NO 5
<211> LENGTH: 28
<212> TYPE: DNA
<213> ORGANISM: artificial
<220> FEATURE:
<223> OTHER INFORMATION: primer

<400> SEQUENCE: 5
ggctaagaag tatggtcctg ttgtaaga                                   28

<210> SEQ ID NO 6
<211> LENGTH: 25
<212> TYPE: DNA
<213> ORGANISM: artificial
<220> FEATURE:
<223> OTHER INFORMATION: primer

<400> SEQUENCE: 6
ggtggacatc aggaacttct tgact                                      25

<210> SEQ ID NO 7
<211> LENGTH: 23
<212> TYPE: DNA
<213> ORGANISM: artificial
```

```
<220> FEATURE:
<223> OTHER INFORMATION: primer

<400> SEQUENCE: 7
agaagtatgg acctgttgtg cgg                                              23

<210> SEQ ID NO 8
<211> LENGTH: 26
<212> TYPE: DNA
<213> ORGANISM: artificial
<220> FEATURE:
<223> OTHER INFORMATION: primer

<400> SEQUENCE: 8
tggttgacat caggaacttc ttaacc                                           26

<210> SEQ ID NO 9
<211> LENGTH: 21
<212> TYPE: DNA
<213> ORGANISM: artificial
<220> FEATURE:
<223> OTHER INFORMATION: primer

<400> SEQUENCE: 9
cacaccgtcg ccaaagagac a                                                21

<210> SEQ ID NO 10
<211> LENGTH: 21
<212> TYPE: DNA
<213> ORGANISM: artificial
<220> FEATURE:
<223> OTHER INFORMATION: primer

<400> SEQUENCE: 10
ggcagcaaca tgccgtagtc a                                                21

<210> SEQ ID NO 11
<211> LENGTH: 25
<212> TYPE: DNA
<213> ORGANISM: artificial
<220> FEATURE:
<223> OTHER INFORMATION: primer

<400> SEQUENCE: 11
agccgtcatc atggaaggtt tctat                                            25

<210> SEQ ID NO 12
<211> LENGTH: 22
<212> TYPE: DNA
<213> ORGANISM: artificial
<220> FEATURE:
<223> OTHER INFORMATION: primer

<400> SEQUENCE: 12
gaactcatcg tgcacatggc aa                                               22

<210> SEQ ID NO 13
<211> LENGTH: 22
<212> TYPE: DNA
<213> ORGANISM: artificial
<220> FEATURE:
<223> OTHER INFORMATION: primer

<400> SEQUENCE: 13
ggcgaccaga cttggaacag ac                                               22
```

```
<210> SEQ ID NO 14
<211> LENGTH: 25
<212> TYPE: DNA
<213> ORGANISM: artificial
<220> FEATURE:
<223> OTHER INFORMATION: primer

<400> SEQUENCE: 14
tggatgacgt aagagatctg ctgtg                                      25

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
cggggctggg aggtcagtat                                            20

<210> SEQ ID NO 16
<211> LENGTH: 22
<212> TYPE: DNA
<213> ORGANISM: artificial
<220> FEATURE:
<223> OTHER INFORMATION: primer

<400> SEQUENCE: 16
gcacgctggt gttttggtg ta                                          22

<210> SEQ ID NO 17
<211> LENGTH: 26
<212> TYPE: DNA
<213> ORGANISM: artificial
<220> FEATURE:
<223> OTHER INFORMATION: primer

<400> SEQUENCE: 17
tggcaaaact attctcacaa aggaag                                     26

<210> SEQ ID NO 18
<211> LENGTH: 25
<212> TYPE: DNA
<213> ORGANISM: artificial
<220> FEATURE:
<223> OTHER INFORMATION: primer

<400> SEQUENCE: 18
agggtcatgt tctgctccaa aatta                                      25

<210> SEQ ID NO 19
<211> LENGTH: 26
<212> TYPE: DNA
<213> ORGANISM: artificial
<220> FEATURE:
<223> OTHER INFORMATION: primer

<400> SEQUENCE: 19
gagatacctg cacctttgtc ctactt                                     26

<210> SEQ ID NO 20
<211> LENGTH: 22
<212> TYPE: DNA
<213> ORGANISM: artificial
<220> FEATURE:
<223> OTHER INFORMATION: primer

<400> SEQUENCE: 20
```

```
gttcttggct gtcattctgg ct                                           22

<210> SEQ ID NO 21
<211> LENGTH: 24
<212> TYPE: DNA
<213> ORGANISM: artificial
<220> FEATURE:
<223> OTHER INFORMATION: primer

<400> SEQUENCE: 21
ccccacattc actcttgacg ctct                                         24

<210> SEQ ID NO 22
<211> LENGTH: 19
<212> TYPE: DNA
<213> ORGANISM: artificial
<220> FEATURE:
<223> OTHER INFORMATION: primer

<400> SEQUENCE: 22
gctggcggac gcctgacat                                               19

<210> SEQ ID NO 23
<211> LENGTH: 23
<212> TYPE: DNA
<213> ORGANISM: artificial
<220> FEATURE:
<223> OTHER INFORMATION: primer

<400> SEQUENCE: 23
caacccctgc ttccgttatc caa                                          23

<210> SEQ ID NO 24
<211> LENGTH: 24
<212> TYPE: DNA
<213> ORGANISM: artificial
<220> FEATURE:
<223> OTHER INFORMATION: primer

<400> SEQUENCE: 24
gagaacaggc gagacacgat ggac                                         24

<210> SEQ ID NO 25
<211> LENGTH: 23
<212> TYPE: DNA
<213> ORGANISM: artificial
<220> FEATURE:
<223> OTHER INFORMATION: primer

<400> SEQUENCE: 25
caatatgcca actccacggt cac                                          23

<210> SEQ ID NO 26
<211> LENGTH: 20
<212> TYPE: DNA
<213> ORGANISM: artificial
<220> FEATURE:
<223> OTHER INFORMATION: primer

<400> SEQUENCE: 26
ggtcgcactg ggtcgaacaa                                              20

<210> SEQ ID NO 27
<211> LENGTH: 24
<212> TYPE: DNA
<213> ORGANISM: artificial
```

```
<220> FEATURE:
<223> OTHER INFORMATION: primer

<400> SEQUENCE: 27
tctccaatct cgtgccgtat ctga                                              24

<210> SEQ ID NO 28
<211> LENGTH: 26
<212> TYPE: DNA
<213> ORGANISM: artificial
<220> FEATURE:
<223> OTHER INFORMATION: primer

<400> SEQUENCE: 28
ctgatgccac ttccatgaca aagtct                                            26

<210> SEQ ID NO 29
<211> LENGTH: 21
<212> TYPE: DNA
<213> ORGANISM: artificial
<220> FEATURE:
<223> OTHER INFORMATION: primer

<400> SEQUENCE: 29
tcgccgagag ctgattggca t                                                 21

<210> SEQ ID NO 30
<211> LENGTH: 23
<212> TYPE: DNA
<213> ORGANISM: artificial
<220> FEATURE:
<223> OTHER INFORMATION: primer

<400> SEQUENCE: 30
cccttcatcc ccgactccct gta                                               23

<210> SEQ ID NO 31
<211> LENGTH: 24
<212> TYPE: DNA
<213> ORGANISM: artificial
<220> FEATURE:
<223> OTHER INFORMATION: primer

<400> SEQUENCE: 31
gtcacattgc tgacaggatg ccta                                              24

<210> SEQ ID NO 32
<211> LENGTH: 21
<212> TYPE: DNA
<213> ORGANISM: artificial
<220> FEATURE:
<223> OTHER INFORMATION: primer

<400> SEQUENCE: 32
gggttggttg ctttgccact c                                                 21
```

US 8,198,257 B2

CYP46A1 GENE FOR THE TREATMENT OF ALZHEIMER'S DISEASE

CROSS-REFERENCE TO RELATED APPLICATIONS

This application is a National Stage application of International Patent Application No. PCT/EP2008/062047, filed on Sep. 11, 2008 and incorporated herein in its entirety, which claims the benefit of U.S. Provisional Application 60/971,624, filed Sep. 12, 2007.

INCORPORATION OF SEQUENCE LISTING

A paper copy of the Sequence Listing named "BET10P0153 Seq List.pdf", which is 216606 bytes in size and which is identical to the Sequence Listing in International Patent Application No. PCT/EP2008/062047, filed on Sep. 11, 2008, is electronically filed herewith and is herein incorporated by reference. This Sequence Listing consists of SEQ ID NOs: 1-32.

FIELD OF THE INVENTION

The present invention relates to the use of the CYP46A1 gene for the treatment of Alzheimer's disease. More precisely, the invention relates to the use of a viral vector, preferably an adenovirus-associated virus (AAV) vector for the transfer of the CYP46A1 gene into the brain of a patient affected with Alzheimer's disease.

BACKGROUND OF THE INVENTION

Alzheimer's disease (AD) is the most prevalent form of all neurodegenerative disorders. Approximately 100,000 victims die and 360,000 new cases of Alzheimer's disease are diagnosed each year. To date, there is no effective treatment for Alzheimer's disease. Research has suggested a number of possible approaches to treatment, such as Cholinergic strategies: Acetylcholinesterase inhibitors (e.g., Tacrine®, Cognex®, or Exelon®) and MI muscarinic receptor agonists; Neurotrophic factors (e.g., Nerve growth factor); Inhibitors of oxidation (e.g., vitamin E); Metal chelating agents; Immunotropic drugs; Non-narcotic analgesics (e.g., Ibuprofen); Inhibitors of beta-A4 aggregation; Estrogen, etc. But so far, none of these approaches has been clearly demonstrated to cause a significant improvement in the majority of patients afflicted with Alzheimer's disease. Thus, a long felt and high medical need exists for new drugs with a novel mode of action for the treatment of Alzheimer's Disease.

The precise mechanisms leading to AD are not completely understood, but since the isolation of the E4 isoform of ApoE as the most significant risk factor of AD (Strittmatter, W. J. et al., 1993), a mechanistic link has been established between cholesterol metabolism and the formation of amyloid plaques. In humans, high level of cholesterol at mid-age is associated with a higher risk of AD (Kivipelto, M. et al, 2002) and cholesterol concentrations are increased in AD brains (Cutler, R. G. et al., 2004). ApoE which binds cholesterol and could regulate lipid transport into neurons is found in senile plaques (Namba, Y. et al., 1991), along with cholesterol itself (Mori, T. et al., 2001). In Niemann-Pick disease type C, due to a mutation of the gene NPC1 that encodes a protein implicated in intracellular transport of cholesterol to post-lysosomal destinations, cholesterol accumulates in neurons together with Aβ peptide in late endosomes (Jin, L. W. et al., 2004). In mouse model of AD, dietary cholesterol accelerates Aβ deposition whereas cholesterol-lowering drugs lower it (Refolo, L. M. et al., 2001). Inhibition of acyl-coenzyme A cholesterol acyltransferase (ACAT), an enzyme that controls the equilibrium between free cholesterol and cholesteryl esters was shown to reduce amyloid pathology (Hutter-Paier, B. et al., 2004). However, inactivation of genes involved in the transport of cholesterol (ApoE, ABCA1 and LDL receptor) in various transgenic AD mice has led to divergent results, likely because changes in cholesterol metabolism were also induced during development, causing uncontrollable compensatory mechanisms. In vitro, changes in the cholesterol content of the membrane induces parallel changes in Aβ secretion (Simons, M. et al, 1998, Ehehalt, R., et al., 2003). It is believed that this modulation occurs at the levels of lipid rafts. A high cholesterol content could facilitate the clustering of β secretase embedded in rafts with APP (Ehehalt, R., et al., 2003); translocation of the γ-secretase complex to the raft could have a similar consequence (Vetrivel, K. S. et al., 2005). On the other hand, there is a negative feedback mechanism between APP processing and neuronal lipid metabolism since Aβ40 inhibits HMG-CoA reductase activity and thus cholesterol synthesis (Grimm, M. O. et al., 2005).

International patent application WO2004/055201 describes cholesterol 24-hydroxylase as a therapeutic target for the treatment of Alzheimer's disease.

The cholesterol 24-hydroxylase is a neuronal enzyme that is coded by the CYP46A1 gene. It converts cholesterol into 24-hydroxycholesterol and has a critical role in the efflux of cholesterol from the brain (Dietschy, J. M. et al., 2004). Brain cholesterol is essentially produced—but cannot be degraded—in situ, and intact blood-brain barrier restricts direct transportation of cholesterol from the brain (Dietschy, J. M. et al., 2004). 24-hydroxycholesterol is able to cross the plasma membrane and the blood-brain barrier and reaches the liver where it is degraded. During the early stages of AD, 24-hydroxycholesterol concentrations are high in CSF and in peripheral circulation. In later stages of AD, concentrations of 24-hydroxycholesterol may fall likely reflecting neuronal loss (Kolsch, H. et al., 2004). CYP46A1 is expressed around the amyloid core of the neuritic plaques in the brain of AD patients (Brown, J., 3rd et al., 2004).

SUMMARY OF THE INVENTION

The present invention provides a viral vector for treating Alzheimer's disease, which vector comprises a cholesterol 24-hydroxylase encoding nucleic acid.

The viral vector preferably comprises a nucleic acid sequence that encodes the amino acid sequence SEQ ID NO:2. More preferably the viral vector comprises sequence SEQ ID NO:1. In a preferred embodiment, the viral vector may be an Adeno-Associated-Virus (AAV) vector, preferably an AVV5 vector. The vector may be useful for the manufacture of a pharmaceutical composition for the treatment of Alzheimer's disease in a subject, wherein the vector is to be administered directly into the brain of the subject, or by intravenous or intrathecal injection.

Preferably the vector may be administered to the ruber nucleus, corpus amygdaloideum, entorhinal cortex and neurons in ventralis lateralis, or to the anterior nuclei of the thalamus, by stereotaxic microinjection.

DETAILED DESCRIPTION OF THE INVENTION

The inventors demonstrated that delivering an adeno-associated vector expressing a CYP46A1 gene into the brain of APP23 mice, a mouse model of Alzheimer's disease, resulted in a marked decrease of neuropathology and an improvement of cognitive deficits.

On this basis, the inventors provide a viral vector for the treatment of Alzheimer's disease, wherein the vector expresses CYP46A1 in cells of the central nervous system.

The CYP46A1 Sequences

The term "gene" refers to a polynucleotide containing at least one open reading frame that is capable of encoding a particular polypeptide or protein after being transcribed or translated.

The terms "coding sequence" or "a sequence which encodes a particular protein", denotes a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic mRNA, genomic DNA sequences from prokaryotic or eukaryotic DNA, and even synthetic DNA sequences.

The CYP46A1 gene encodes cholesterol 24-hydroxylase. This enzyme is a member of the cytochrome P450 superfamily of enzymes. A cDNA sequence for CYP46A1 is disclosed in Genbank Access Number NM_006668 (SEQ ID NO:1). The amino acid sequence is shown in SEQ ID NO:2.

The invention makes use of a nucleic acid construct comprising sequence SEQ ID NO:1 or a variant thereof for the treatment of Alzheimer's disease.

The variants include, for instance, naturally-occurring variants due to allelic variations between individuals (e.g., polymorphisms), alternative splicing forms, etc. The term variant also includes CYP46A1 gene sequences from other sources or organisms. Variants are preferably substantially homologous to SEQ ID NO:1, i.e., exhibit a nucleotide sequence identity of typically at least about 75%, preferably at least about 85%, more preferably at least about 90%, more preferably at least about 95% with SEQ ID NO:1. Variants of a CYP46A1 gene also include nucleic acid sequences, which hybridize to a sequence as defined above (or a complementary strand thereof) under stringent hybridization conditions. Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

The Viral Vectors

Gene delivery viral vectors useful in the practice of the present invention can be constructed utilizing methodologies well known in the art of molecular biology. Typically, viral vectors carrying transgenes are assembled from polynucleotides encoding the transgene, suitable regulatory elements and elements necessary for production of viral proteins which mediate cell transduction.

The terms "gene transfer" or "gene delivery" refer to methods or systems for reliably inserting foreign DNA into host cells. Such methods can result in transient expression of non integrated transferred DNA, extrachromosomal replication and expression of transferred replicons (e.g., episomes), or integration of transferred genetic material into the genomic DNA of host cells.

Examples of viral vector include adenoviral, retroviral, herpesvirus and adeno-associated virus (AAV) vectors.

Such recombinant viruses may be produced by techniques known in the art, such as by transfecting packaging cells or by transient transfection with helper plasmids or viruses. Typical examples of virus packaging cells include PA317 cells, Psi-CRIP cells, GPenv+ cells, 293 cells, etc. Detailed protocols for producing such replication-defective recombinant viruses may be found for instance in WO95/14785, WO96/22378, U.S. Pat. No. 5,882,877, U.S. Pat. No. 6,013,516, U.S. Pat. No. 4,861,719, U.S. Pat. No. 5,278,056 and WO94/19478.

In a preferred embodiment, adeno-associated viral (AAV) vectors are employed. In a more preferred embodiment, the AAV vector is an AAV5.

By an "AAV vector" is meant a vector derived from an adeno-associated virus serotype, including without limitation, AAV-1, AAV-2, AAV-3, AAV-4, AAV-5, AAV6, AAV9, AAV10 etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. AAV expression vectors are constructed using known techniques to at least provide as operatively linked components in the direction of transcription, control elements including a transcriptional initiation region, the DNA of interest (i.e. the CYP46A1 gene) and a transcriptional termination region.

The control elements are selected to be functional in a mammalian cell. The resulting construct which contains the operatively linked components is bounded (5' and 3') with functional AAV ITR sequences. By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome. The nucleotide sequences of AAV ITR regions are known. See, e.g., Kotin, 1994; Berns, K I "Parvoviridae and their Replication" in Fundamental Virology, 2nd Edition, (B. N. Fields and D. M. Knipe, eds.) for the AAV-2 sequence. As used herein, an "AAV ITR" does not necessarily comprise the wild-type nucleotide sequence, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV6, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

Particularly preferred are vectors derived from AAV serotypes having tropism for and high transduction efficiencies in cells of the mammalian CNS, particularly neurons. A review and comparison of transduction efficiencies of different serotypes is provided in Davidson et al., 2000. In one preferred example, AAV2 based vectors have been shown to direct long-term expression of transgenes in CNS, preferably transducing neurons. In other non-limiting examples, preferred vectors include vectors derived from AAV4 and AAV5 serotypes, which have also been shown to transduce cells of the CNS (Davidson et al, supra). In particular, the vector may be an AAV vector comprising a genome derived from AAV5 (in particular the ITRs are AAV5 ITRs) and a capsid derived from AAV5.

In a particular embodiment of the invention, the vector is a pseudotyped AAV vector. Specifically, a pseudotyped AAV vector comprises an AAV genome derived from a first AAV serotype and a capsid derived from a second AAV serotype. Preferably, the genome of the AAV vector is derived from AAV2. Furthermore, the capsid is preferably derived from AAV5. Specific non-limiting examples of pseudotyped AAV vectors include an AAV vector comprising a genome derived from AAV2 in a capsid derived from AAV5, an AAV vector comprising a genome derived from AAV2 in a capsid derived from AAV10, etc.

The selected nucleotide sequence is operably linked to control elements that direct the transcription or expression thereof in the subject in vivo. Such control elements can comprise control sequences normally associated with the selected gene. In particular, such control elements may include the promoter of the CYP46A1 gene, in particular the promoter of the human CYP46A1 gene (Ohyama Y et al., 2006)

Alternatively, heterologous control sequences can be employed. Useful heterologous control sequences generally include those derived from sequences encoding mammalian or viral genes. Examples include, but are not limited to, the phophoglycerate kinase (PKG) promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.). For purposes of the present invention, both heterologous promoters and other control elements, such as CNS-specific and inducible promoters, enhancers and the like, will be of particular use.

Examples of heterologous promoters include the CMV promoter. Examples of CNS specific promoters include those isolated from the genes from myelin basic protein (MBP), glial fibrillary acid protein (GFAP), and neuron specific enolase (NSE).

Examples of inducible promoters include DNA responsive elements for ecdysone, tetracycline, hypoxia andaufin.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994. Alternatively, AAV ITRs can be excised from the viral genome or from an AAV vector containing the same and fused 5' and 3' of a selected nucleic acid construct that is present in another vector using standard ligation techniques. AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV ITR sequences arranged 5' and 3' of one or more selected nucleic acid sequences. Preferred codons for expression of the chimeric gene sequence in mammalian CNS cells can be used. The complete chimeric sequence is assembled from overlapping oligonucleotides prepared by standard methods. See, e.g., Edge, 1981; Nambair et al., 1984; Jay et al., 1984. In order to produce rAAV virions, an AAV expression vector is introduced into a suitable host cell using known techniques, such as by transfection. A number of transfection techniques are generally known in the art. See, e.g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Feigner et al., 1987), and nucleic acid delivery using high-velocity microprojectiles (Klein et al., 1987).

For instance, a preferred vector, such as the AVV5-CYPwt used in the below examples, comprises, in addition to a cholesterol 24-hydroxylase encoding nucleic acid sequence, the backbone of AAV vector with ITR derived from AAV-5, the promoter of the mouse PGK (phosphoglycerate kinase) gene, and the woodchuck hepatitis virus post-transcriptional regulatory element (WPRE).

Delivery of the Viral Vectors

It is herein provided a method for treating Alzheimer's disease in a subject, said method comprising:
(a) providing a viral vector as defined above, which comprises a cholesterol 24-hydroxylase encoding nucleic acid; and
(b) delivering the viral vector to the central nervous system (CNS) of the subject, whereby said vector transduces cells in the CNS, and whereby cholesterol 24-hydroxylase is expressed by the transduced cells at a therapeutically effective level.

It is further provided the use of a vector as defined above, which comprises a cholesterol 24-hydroxylase encoding nucleic acid, for the manufacture of a pharmaceutical composition for the treatment of Alzheimer's disease in a subject, wherein the vector is to be delivered to the central nervous system (CNS) of the subject, preferably directly into the brain of the subject or by intravenous or intrathecal injection.

It is also provided the vector as defined above, which comprises a cholesterol 24-hydroxylase encoding nucleic acid, for the treatment of Alzheimer's disease in a subject, wherein the vector is to be delivered to the central nervous system (CNS) of the subject, preferably directly into the brain of the subject or by intravenous or intrathecal injection.

Methods of delivery of viral vectors to neurons and/or astrocytes includes generally any method suitable for delivery vectors to the neurons and/or astrocytes such that at least a portion of cells of a selected synaptically connected cell population is transduced. The vector may be delivered to any cells of the central nervous system, cells of the peripheral nervous system, or both. Generally, the vector is delivered to the cells of the central nervous system, including for example cells of the spinal cord, brainstem (medulla, pons, and midbrain), cerebellum, diencephalon (thalamus, hypothalamus), telencephalon (corpus striatum, cerebral cortex, or, within the cortex, the occipital, temporal, parietal or frontal lobes), or combinations thereof, or preferably any suitable subpopulation thereof. Further preferred sites for delivery include the ruber nucleus, corpus amygdaloideum, entorhinal cortex and neurons in ventralis lateralis, or to the anterior nuclei of the thalamus.

To deliver the vector specifically to a particular region and to a particular population of cells of the CNS, the vector may be administered by stereotaxic microinjection. For example, patients have the stereotactic frame base fixed in place (screwed into the skull). The brain with stereotactic frame base (MRIcompatible with fiducial markings) is imaged using high resolution MRI. The MRI images are then transferred to a computer which runs stereotactic software. A series of coronal, sagittal and axial images are used to determine the target (site of AAV vector injection) and trajectory. The software directly translates the trajectory into 3 dimensional coordinates appropriate for the stereotactic frame. Burr holes are drilled above the entry site and the stereotactic apparatus positioned with the needle implanted at the given depth. The AAV vector is then injected at the target sites. Since the AAV vector integrates into the target cells, rather than producing viral particles, the subsequent spread of the vector is minor, and mainly a function of passive diffusion from the site of injection and of course the desired transsynaptic transport, prior to integration. The degree of diffusion may be controlled by adjusting the ratio of vector to fluid carrier.

Additional routes of administration may also comprise local application of the vector under direct visualization, e.g., superficial cortical application, or other nonstereotactic application. The vector may generally be delivered intrathecally, for specific applications.

The target cells of the vectors of the present invention are cells of the central nervous systems of a subject afflicted with Alzheimer's disease, preferably neural cells. Preferably the subject is a human being, generally an adult.

However the invention encompasses delivering the vector to biological models of the disease. In that case, the biological model may be any mammal at any stage of development at the time of delivery, e.g., embryonic, fetal, infantile, juvenile or adult, preferably it is an adult. Furthermore, the target CNS cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e.g. zebrafish model system).

Preferably, the method of the invention comprises intracerebral administration, e.g. directly into the cerebral ventricles.

However, other known delivery methods may also be adapted in accordance with the invention. For example, for a more widespread distribution of the vector across the CNS, it may be injected into the cerebrospinal fluid, e.g., by lumbar puncture. To direct the vector to the peripheral nervous system, it may be injected into the spinal cord or into the peripheral ganglia, or the flesh (subcutaneously or intramuscularly) of the body part of interest. In certain situations the vector can be administered via an intravascular approach. For example, the vector can be administered intra-arterially (carotid) in situations where the blood-brain barrier is disturbed. Moreover, for more global delivery, the vector can be administered during the "opening" of the blood-brain barrier achieved by infusion of hypertonic solutions including mannitol.

The viral vectors used herein may be formulated in any suitable vehicle for delivery. For instance they may be placed into a pharmaceutically acceptable suspension, solution or emulsion. Suitable mediums include saline and liposomal preparations. More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Intravenous vehicles include fluid and nutrient replenishers, electrolyte replenishers (such as those based on Ringer's dextrose), and the like.

Preservatives and other additives may also be present such as, for example, antimicrobials, antioxidants, chelating agents, and inert gases and the like. A colloidal dispersion system may also be used for targeted gene delivery.

Colloidal dispersion systems include macromolecule complexes, nanocapsules, microspheres, beads, and lipid-based systems including oil-in-water emulsions, micelles, mixed micelles, and liposomes.

The preferred doses and regimen may be determined by a physician, and depend on the age, sex, weight, of the subject, and the stage of the disease. As an example, for delivery of cholesterol 24-hydroxylase using a viral expression vector, each unit dosage of cholesterol 24-hydroxylase expressing vector may comprise 2.5 to 25 µl of a composition including a viral expression vector in a pharmaceutically acceptable fluid and which provides from $10^{10}$ up to $10^{15}$ cholesterol 24-hydroxylase expressing viral particles per ml of composition.

The figures and examples illustrate the invention without limiting its scope.

LEGENDS TO THE FIGURES

FIGS. 1A to 1C show that the expression of mutant form of APP in murine neuronal cell results in the production of Aβ peptides and down-regulation of CYP46A1 gene. FIG. 1A is a graph, accompanied by a Western blot, that shows expression of Aβ40 peptide in various neuroblastoid cell lines. FIG. 1B is a Western blot that shows that expression of CYP46A1 is abolished in neuroblastoid cell line expressing mutant form of APP. FIG. 1C is a graph showing reduction of the level of 24S-hydroxycholesterol in the N2A-hAPPsI cell line expressing mutant form of APP.

FIG. 2A is a graph showing that transient re-expression of CYP46A1 gene in murine neuronal cell line expressing mutant form of APP results in decreased secretion of Aβ40 and Aβ42 peptides. FIGS. 2B, 2C and 2D are graphs showing that stable re-expression of CYP46A1 gene in murine neuronal cell line expressing mutant form of APP results in decreased secretion of Aβ40 and Aβ42 peptides in a gene-dose-dependant manner, with an increase of 24S-hydroxycholesterol but without change in cholesterol content.

FIG. 3 is a graph that shows that expression of CYP46A1 in the brain of APP mice results in an increase of 24-hydroxycholesterol.

FIG. 4 shows amyloid plaques in the hippocampus of APP mice. Expression of CYP46A1 results in decreased number of amyloid plaques in APP mice FIGS. 5A to 5C show a comparison of APP transgenic mice treated with AAV-CYPPmt and mice treated with AAV-CYP-Pwt in the acquisition phase (path length and escape latency) (FIG. 5A), swim speed (FIG. 5B) and probe trial (FIG. 5C).

Figure 6:
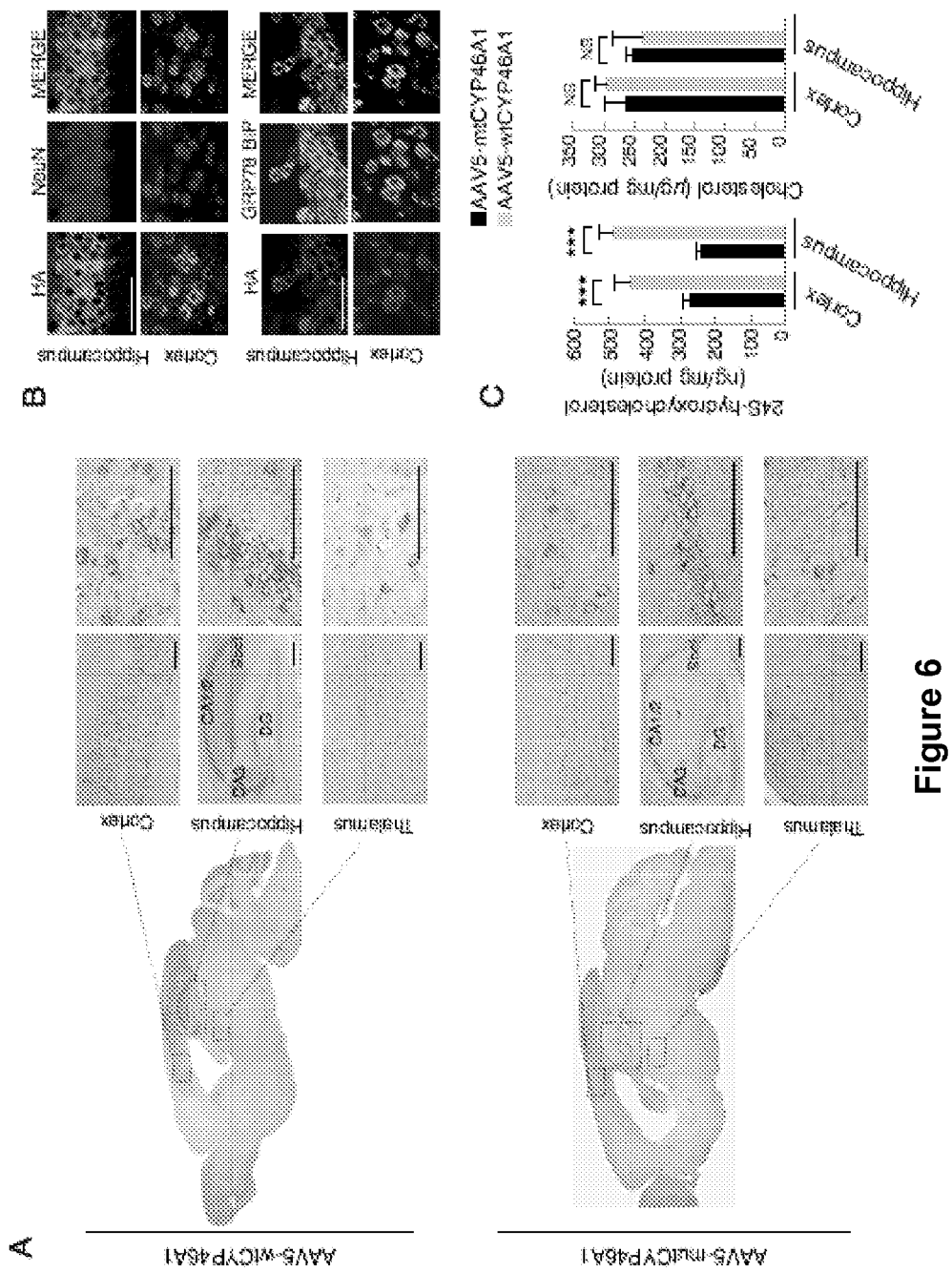

FIG. 6A to 6C show that injections of AAV5-CYP46A1 vector in cerebral cortex and hippocampus increases the levels of 24S-hydroxycholesterol. (A) Representative expression of the wild-type (wtCYP46A1) and mutant (mtCYP46A1) forms of human CYP46A1 protein in the brain of 12-month-old APP23 mice after injection of AAV vector. DG: dentate gyrus; Sbcl: Subiculum; CA: Cornu Ammonis. Scale bar=200 µM. (B) Immunolabelling of HA-tagged wtCYP46A1 protein in neurons (NeuN, nuclear staining, upper panel) and co-localization with the endoplasmic reticulum Grp78 Bip marker (lower panel). HA-tagged mtCYP46 protein has identical subcellular localization (not shown). Scale bar=200 µM. (C) Cholesterol and 24S-hydroxycholesterol concentrations in the cerebral cortex and hippocampus of 12-month-old APP23 mice injected with AAV5-wtCYP46A1 or AAV5-mtCYP46A1 vectors (n=5 mice per group). (Mann-Whitney U-test) *** P<0.0005; NS: non significant.

FIGS. 7A to 7G show that intracerebral delivery of CYP46A1 markedly reduces amyloid pathology in APP23 mice. (A) Representative immunostaining of amyloid deposits with NT2 antibody in 12-month-old APP23 mice injected with AAV5-mtCYP46A1 (upper panel) or AAV5-wtCYP46A1 (lower panel) vectors. Scale bar=200 µM. (B) Stereological analyses of amyloid deposit number and surface in the cortex and hippocampus of APP23 mice injected with AAV5-mtCYP46A1 or AAV5-wtCYP46A1 vectors at 12 months (3 different section levels per mouse, with 3-5 slices per level, n=mice per group). (C) $A\beta_{40}$ and $A\beta_{42}$ peptide concentrations in the pooled cerebral cortex and hippocampus of 12-month-old APP23 mice injected with AAV5-wtCYP46A1 or AAV5-mtCYP46A1 vectors. $A\beta$ peptides were quantified using ELISA after a solubilization step in 5M guanidine-HCl (n=5 mice per group). (D) Quantification of mono-, tri-, hexa- and dodecamers of $A\beta$ peptides by Western blotting after extraction in mM Tris-HCl (Tris), 10 mM Tris-HCl/2% Triton (Triton) and 10 mM Tris-HCl/0.5% SDS (SDS) buffers (n=5 mice per group). (E) Representative Western blot of full length APP (APPfl), BACE1, PSEN1 and CTFs (C83, C99 and AICD) in pooled cerebral cortex and hippocampus samples from 12-month-old APP23 mice injected with AAV5-wt-CYP46A1 and AAV5-mtCYP46A1 vectors (n=5 mice per group). (F) Quantification of α- and β-secretases C-terminal fragments (C83 and C99) in pooled cerebral cortex and hippocampus samples from 12-month-old APP23 mice injected with AAV5-wt-CYP46A1 and AAV5-mtCYP46A1 vectors. The amounts of C-terminal fragments are normalized to ACTIN level (n=5 mice per group). A.U: arbitrary unit. (G) Quantitative expression of murine 3-hydroxy-3-methylglutaryl-Coenzyme A reductase (Hmgcr), sterol-binding protein 2 (Srebp2), acyl-coenzyme A: cholesterol acyltransferase 1 (Acat1), Cyp46A1 and Cyp27A1 genes in APP23 mice injected with AAV5-wtCYP46A1 or AAV5-mtCYP46A1 vectors (n=5 mice per group). (Mann-Whitney U-test). * P<0.05; ** P<0.005. A.U=arbitraty units.

FIGS. 8A to 8E show that decreased microgliosis and improvement of cognitive performances is observed in APP23 mice treated with AAV5-wtCYP46A1 vector. (A, B) Number of Iba-1 positive cells in the cortex, hippocampus and cerebellum of APP23 mice injected with AAV5-wtCYP46A1 or AAV5-mutCYP46A1 vectors. Scale bar=100 µM. (n=5 mice per group; 3 section levels per mouse were analyzed). (Mann-Whitney U-test). * P<0.05; NS: not significant. (C) Path length, (D) escape latency, (E) swim speed curves during the acquisition phase of the Morris water maze procedure in APP23 mice treated with the AAV5-wtCYP46A1 (n=5, open symbols) or AAV-mutCYP46A1 (control) vectors (n=4, closed circles). Data points represent mean (±SEM) summed results of four daily trials. (F) This panel represents the proportion of total time spent in each quadrant of the Morris water maze during probe trial in APP23 mice treated with the control versus the therapeutic vectors. Bars represent mean (SEM) percentage of total time in a specific quadrant.

FIGS. 9A to 9D show that the expression of CYP46A1 gene decreases $A\beta_{40/42}$ peptide secretion in murine neuroblastoid N2a cells expressing mutated human APP (APPsI). (A) Secretion of $A\beta_{40}$ and $A\beta_{42}$ peptides and mRNA/protein levels of APPsI in N2a and N2a-hAPPsI cell lines (clones 11, 12 and 17). A weak signal corresponding to the non-mutated murine APP protein is detected in N2a cells. (B) Intracellular level of cholesterol and 24S-hydroxycholesterol in N2a and N2a-APP17 cells. (C) Intracellular levels of cholesterol and 24S-hydroxycholesterol in two N2a-APP17 clones expressing the human CYP46A1 gene (N2a-APP-CYP-A, and -B). (D) Decreased secretion of $A\beta_{40/42}$ peptides in N2a-APP-CYP-A and -B cells. The amounts of secreted $A\beta_{40/42}$ peptides are normalized to 100% in N2a-APP17 cells. All experiments were done in triplicate. (ANOVA and post-hoc Student's t-test) * P<0.05;  P<0.005; * P<0.0005; NS: non significant.

Figure 10:
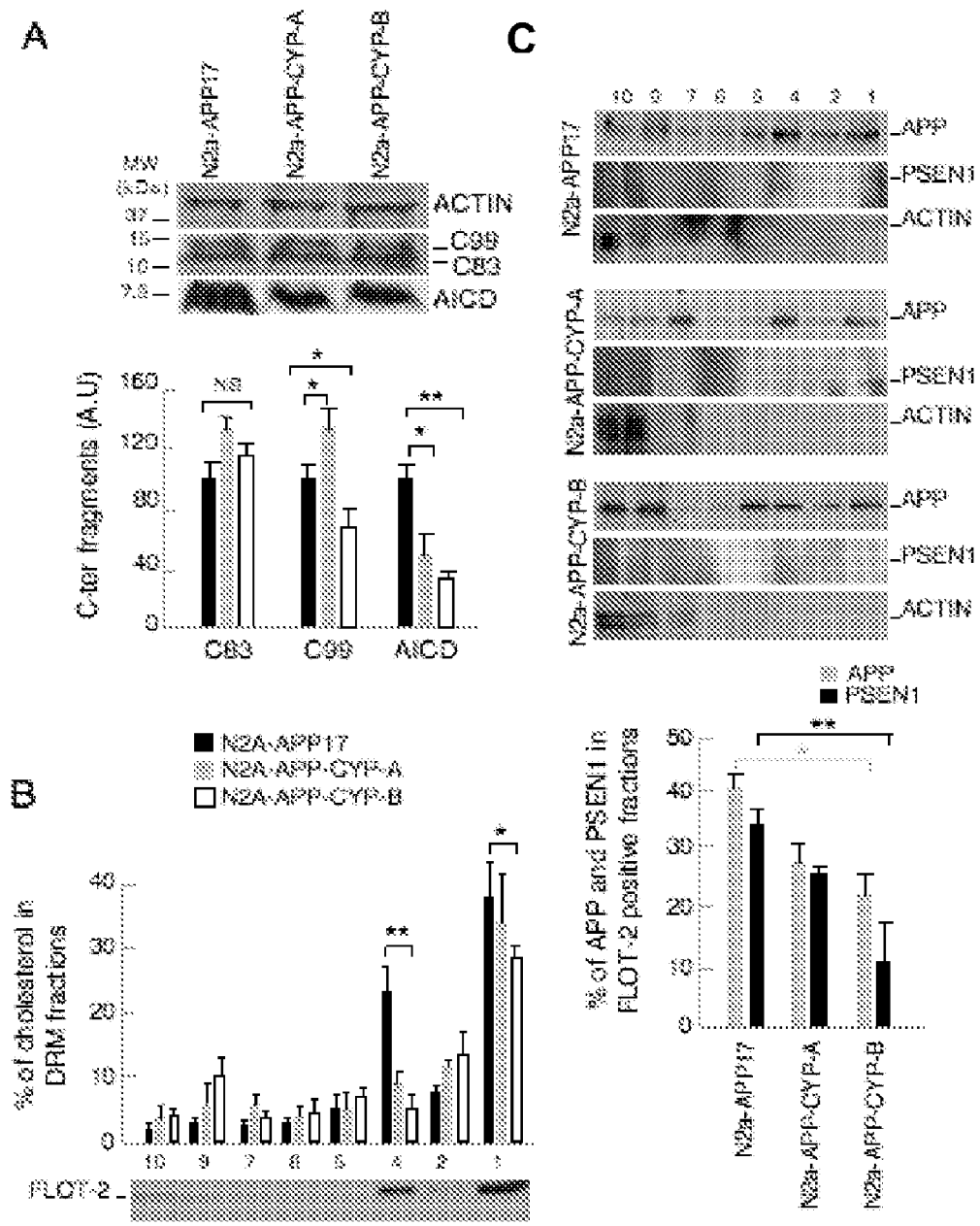

FIGS. 10A to 10C relates to the quantification of C-terminal fragments in N2a-APP17 cells expressing the cholesterol 24-hydroxylase gene and measurement of cholesterol, APP and PSEN1 in detergent resistant membrane (DRM). (A) Representative Western blot and quantification of α-, β- and γ-secretase C-terminal fragments (C83, C99 and AICD) in crude extracts from N2a-APP17, N2a-APP-CYP-A and N2a-APP-CYP-B cells. Dark bars: N2a-APP17; grey bars: N2a-APP-CYP-A; open bars: N2a-APP-CYP-B. The amounts of C-terminal fragments are normalized to ACTIN level; A.U: arbitrary unit. (B) Cholesterol content in DRMs isolated after iodixanol gradient ultracentrifugation from N2a-APP17, N2a-APP-CYP-A and N2a-APP-CYP-B cells. As expected highest content of cholesterol is found in FLOTILLIN 2 (FLOT-2) positive fractions from N2a-APP17 cells. Dark bars: N2a-APP17; grey bars: N2a-APP-CYP-A; open bars: N2a-APP-CYP-B. (C) Protein blot analysis of APP, BACE1, PSEN1 and FLOT-2 in N2a-APP17, N2a-APP-CYP-A and N2a-APP-CYP-B cells. The percentages of APP and PSEN1 associated with FLOT-2 positive fractions 1 and 4 are shown on the right. All experiments were done in triplicate. (ANOVA and post-hoc Student's t-test) * P<0.05; ** P<0.005; NS: non significant.

EXAMPLES

Materials and Methods

Cell Lines and Culture Conditions

Cells were maintained in Dulbecco's Modified Eagle's medium (DMEM) supplemented with 10% fetal bovine serum, 1% Glutamine and 1% penicillin and streptomycin (all from Gibco laboratories). APPsI (containing the Swedish K670NM671L and London V717I mutations) cDNA was obtained by PCR from APP/PS mice (L. Pradier, Sanofi-Aventis-France) and cloned under a pCMV promoter in a pIRES-PURO plasmid (Invitrogen). After transfection using the Effectene tranfection kit (QIAGEN), puromycin-resistant N2a-hAPPsI cells were selected by limit dilution method and tested by PCR. N2a-APPsI cells were then stably transfected by a pcDNA-pCMV-CYP46A1 plasmid containing a neomycin-resistant selection cassette. CYP46A1 cDNA was generously provided by L. Pradier (Sanofi-Aventis-France).

Determination of Cholesterol and 24S-Hydroxycholesterol

The quantification of cellular cholesterol was performed using the Amplex Red cholesterol assay kit (Invitrogen). For 24S-hydroxycholesterol determination, 24-hydroxycholesterol-$^2H_7$ (Medical Isotopes) internal standard was added to brain and cell-homogenates. After hydrolysis and extraction, samples were sulphatated, and 24S-hydroxycholesterol was quantified by HPLC-tandem mass spectrometry (Quattro II, Micromass, Manchester, UK) using a calibration curve with electrospray ionization (ESI) in the negative ion mode. Samples were loaded onto an analytical column at 0.3 ml/min (Alltima C18, 250×2.1 mm, 5μ Altech). The mobile phase consisted of 0.1% ammonia in MilliQ (A) and acetonitril:$H_2O$, 9:1, v/v (B). The following gradient was run for a total run time of 25 min: 0-10 min 85% A to 50% A, 10-20 min to 100% A, 20-20.1 min to 85% A, 20.1-25 min 85% A. Mass spectrometric parameters were as follows: nitrogen as nebulizing gas; argon as collision gas (2.5×10-3 mBar), collision energy 20 eV, capillary voltage 3 kV, source temperature 80° C. and cone voltage 25 V. The following transitions were used to detect 24S-hydroxycholesterol: m/z 280.1→m/z 97 and m/z 283.6→m/z 97 for the internal standard.

Determination of Aβ Levels by ELISA

In vitro, secreted Aβ peptides were measured in the medium 48 hours after plating the cells. In vivo, dissected cortex and hippocampus were first homogenized in 10 mM Tris-HCl buffer (pH 6.8), adjusted to 6 mg protein/ml and 50 μl was extracted in 5M guanidine-HCl. $A\beta_{40}$ and $A\beta_{42}$ peptides were quantified using commercially available ELISA kits (Biosource and Innogenetics).

Western Blotting

Western blot experiments were performed using a standard protocol (10% PAGE-SDS electrophoresis), excepting for Aβ oligomers analyses that were done using precast CRITERION 12% Bis-Tris gels (BIO-RAD) in NuPAGE MES running buffer (Invitrogen). All samples were extracted in lysis buffer containing protease inhibitor cocktail (Complete, Roche). Primary antibodies (table 1) were incubated for 2 hours at room temperature, followed by species-specific peroxidase-conjugated secondary antibodies. The Enhanced Chemilumninescence method (GE Healthcare) was used for revelation. Signal quantification was done using densitometry analysis of the scanned autoradiograms with the ImageJ 1.38×NIH software.

Soluble Aβ Oligomers Analyses

Dissected cortex and hippocampus were first homogenized in a dounce homogeneizer in Tris-HCl 10 mM, pH 6.8 supplemented with protease inhibitor cocktail (Complete, Roche). Protein concentration was adjusted to 6 mg/ml for all samples. A first ultracentrifugation step (100,000 g at 4° C.) was performed to collect the Tris supernatant and the pellet was dissolved into a Tris-HCl 10 mM, 2% triton buffer (pH 6.8). Another ultracentrifugation step (100,000 g, 4° C.) allowed removing the triton supernatant and the pellet was resuspended in a Tris-HCl 10 mM, 0.5% SDS buffer (pH 6.8). After a last ultracentrifugation step (100,000 g at room temperature), the SDS supernatant was collected and the pellet was directly dissolved in Blue Laemmli solution.

Detergent Resistant Membrane (DRM) Isolation

Lipid rafts were isolated as previously described (Vetrivel et al, 2004). A pellet of ten million cells was first lyzed in MBS buffer (25 mM MES, 150 mM NaCl, EDTA 1 mM pH6.5) containing 1% Triton X-100 and protease inhibitor cocktail (Complete, Roche). All steps were performed at 4° C. The protein concentration was adjusted to 5 mg/ml and cell lysates were brought into 40% iodixanol (OptiPrep Dendity Gradient, Sigma) diluted in appropriate buffer (0.25M sucrose, 6 mM EDTA, 120 mM Tricine, pH7.6). Two layers of 30% and then 20% iodixanol buffer were overlaid at the top of the ultracentrifuge tube. After ultracentrifugation at 39.000 rpm for 20 h at 4° C., fractions (of 1 ml) were collected and analyzed by western blotting according to standard protocol. The detection of flotillin-2 was used to identify DRM fractions.

Quantitative RT-PCR

Messenger RNA extraction from cells or tissues was performed using the RNAble kit (Eurobio laboratories). Real-time quantitative RT-PCR on the ABI Prism 7700 Sequence Detection System (Perkin-Elmer Applied Biosystems) was performed as described (Bieche et al, 2004).

As an endogenous RNA control, we quantified transcripts of the TATA box-binding protein gene (TBP). The amount of target transcript (Ntarget) was normalized based on the basis of the TBP content of each sample and was subsequently normalized to a basal mRNA level with the equation: Ntarget=2ΔCtsample, where ΔCt is the Ct value of the target gene minus the Ct value of the TBP gene. Primers are listed in table 2.

TABLE 1

List of primary antibodies

| Detected Antigen | Antibody | Dilution | Supplier |
|---|---|---|---|
| Amyloid plaques | Mouse monoclonal, clone 4G8 | 1/200 | Chemicon |
| | Rabbit serum NT12 | 1/1000 | Staufenbiel M et al., Novartis |
| Aβ oligomers | Mouse monoclonal, clone 6E10 | 1/1000 | Sigma-Aldrich |
| APPfl | Mouse monoclonal, clone 22C11 | 1/500 | Chemicon |
| APP CTF | Rabbit polyclonal | 1/1000 | Calbiochem |
| BACE-1 | Rabbit polyclonal EE17 | 1/500 | Sigma-Aldrich |
| Presenilin | Rabbit polyclonal | 1/100 | Abcam |
| Flotillin-2 | Mouse monoclonal, clone A-3 | 1/200 | Santa-Cruz biotechnology |
| Hemagglutinin | Mouse monoclonal, clone 16B12 | 1/200 | Covance |
| | Rabbit polyclonal Y-11 | 1/100 | Santa-Cruz biotechnology |
| GRP78 Bip | Rabbit polyclonal | 1/500 | Abcam |
| NeuN, neuron | Mouse monoclonal NeuN biotin | 1/200 | Chemicon |
| Iba1, microglia | Rabbit polyclonal IBA-1 | 1/200 | Wako |
| GFAP, astrocyte | Rabbit polyclonal GFAP | 1/500 | SIGMA-ALDRICH |
| β-actin | Rabbit polyclonal | 1/1000 | Abcam |

TABLE 2

List of primers used for real-time RT-PCR

| Gene | Primer | Sequence |
|---|---|---|
| Tbp | For | tgcacaggagccaagagtgaa (SEQ ID NO: 3) |
|  | Rev | cacatcacagctccccacca (SEQ ID NO: 4) |
| Cyp46a1 | For | ggctaagaagtatggtcctgttgtaaga (SEQ ID NO: 5) |
|  | Rev | ggtggacatcaggaacttcttgact (SEQ ID NO: 6) |
| CYP46A1 | For | agaagtatggacctgttgtgcgg (SEQ ID NO: 7) |
|  | Rev | tggttgacatcaggaacttcttaacc (SEQ ID NO: 8) |
| APP | For | cacaccgtcgccaaagagaca (SEQ ID NO: 9) |
|  | Rev | ggcagcaacatgccgtagtca (SEQ ID NO: 10) |
| Bace1 | For | agccgtcatcatggaaggtttctat (SEQ ID NO: 11) |
|  | Rev | gaactcatcgtgcacatggcaa (SEQ ID NO: 12) |
| Adam9 | For | ggcgaccagacttggaacagac (SEQ ID NO: 13) |
|  | Rev | tggatgacgtaagagatctgctgtg (SEQ ID NO: 14) |
| Adam10 | For | cggggctgggaggtcagtat (SEQ ID NO: 15) |
|  | Rev | gcacgctggtgtttttggtgta (SEQ ID NO: 16) |
| Adam17 | For | tggcaaaactattctcacaaaggaag (SEQ ID NO: 17) |
|  | Rev | agggtcatgttctgctccaaaatta (SEQ ID NO: 18) |
| Psen1 | For | gagatacctgcacctttgtcctactt (SEQ ID NO: 19) |
|  | Rev | gttcttggctgtcattctggct (SEQ ID NO: 20) |
| Hmgcr | For | ccccacattcactcttgacgctct (SEQ ID NO: 21) |
|  | Rev | gctggcggacgcctgacat (SEQ ID NO: 22) |
| Abca1 | For | caaccctgcttccgttatccaa (SEQ ID NO: 23) |
|  | Rev | gagaacaggcgagacacgatggac (SEQ ID NO: 24) |
| Abca2 | For | caatatgccaactccacggtcac (SEQ ID NO: 25) |
|  | Rev | ggtcgcactgggtcgaacaa (SEQ ID NO: 26) |
| Abcg1 | For | tctccaatctcgtgccgtatctga (SEQ ID NO: 27) |
|  | Rev | ctgatgccacttccatgacaaagtct (SEQ ID NO: 28) |
| Abcg4 | For | tcgccgagagctgattggcat (SEQ ID NO: 29) |
|  | Rev | cccttcatccccgactcctgta (SEQ ID NO: 30) |
| ApoE | For | gtcacattgctgacaggatgccta (SEQ ID NO: 31) |
|  | Rev | gggttggttgctttgccactc (SEQ ID NO: 32) |

AAV Plasmid Design and Vectors Production

Wild-type and mutant CYP46A1 pcDNA plasmids were generously given by L. Pradier (Sanofi-Aventis-France). Three PCR-generated fragments containing the entire sequences of the 0.6 kb murine phosphoglycerate kinase (PGK) promoter, the 1.5 kb CYP46A1 cDNA and the 0.6 kb regulatory element of woodchuck hepatitis virus post-transcriptional regulatory element (WPRE) were cloned to generate pAAV5/PGK-hCYP46A1-WPRE plasmids. The functionality of each AAV plasmid was checked by transient transfection of 293T cells. These plasmids were used to generate AAV5/PGK-HACYP46A1 (referred to as AAV5-wtCYP46A1 or AAV5-CYPwt) and AAV5/PGK-HACYP46A1mut (referred to as AAV5-mtCYP46A1 or AAV5-CYPmt) vectors. AAV vector stocks were generated by transient transfection of 293T cells and purified using CsCl ultracentrifugation gradient (Sevin et al, 2006). Titers ranged from 4 to $9.10^{12}$ vg/ml.

Transgenic Mouse Line and Intracerebral Injections of AAV Vectors

The APP23 transgenic mouse line (Thy1-hAPPswe) (Sturchler-Pierrat et al, 1997) was generously provided by Matthias Staufenbiel (Novartis Pharma). These mice overexpress the mutated human $APP_{751}$ gene containing the Swedish double mutation (K670N-M671 L) under the neuronal specific promoter Thy-1. Animals were housed in a pathogen-free animal facility. The experiments were approved by the veterinary desk of INSERM and carried out in compliance with the guide for the Care and Use of Laboratory Animals (NIH publication no. 85-24) and the European communities Council Directive (86/609/EEC). In addition, the behavioural screening protocol was approved by the Animal Ethics Committee of the University of Antwerp. APP23 mice were anesthetized by intraperitoneal injection of ketamine/xylazine (0.1/0.05 mg/g body weight) and positioned on a stereotactic frame (David Kopf Instruments, Tujunga, Calif., USA). Injections of vectors were performed in the cerebral cortex (two deposits) and hippocampus (one deposit) of each hemisphere with 2 μl of viral preparation ($12.10^8$ vg) using a 30-gauge blunt micropipette attached to a 10-μl—Hamilton syringe (Reno, Nev., USA) at a rate of 0.2 μl/min. Stereotactic coordinates of injection sites from bregma were 1/: AP: −0.3; ML: ±2; DV: −1.5 mm; 2) AP: −2; ML: ±1.2; DV: −1.2 mm and AP: −2; ML: ±1.2; DV: −2 mm.

Mice were sacrificed at 6 or 12 months. One half-brain was used for histochemistry. The hippocampus and cerebral cortex of the other half-brain were dissected for biochemistry, gene expression and protein analysis using Western blotting.

Behavioural Analysis

The Morris water maze (MWM) setting consisted of a circular pool (diameter: 150 cm, height: 30 cm) filled with opacified water (non-toxic natural paint), kept at 25° C., and surrounded by invariable visual extramaze cues. A round acrylic glass platform (diameter: 15 cm) was placed 1 cm below the water surface at a fixed position in one of the quadrants. The acquisition phase comprised 8 trial blocks of 4 daily trials semi-randomly starting from four different positions around the border of the maze with 15-min inter-trial intervals. In case a mouse was unable to reach the platform within 120 s, it was placed on the platform during 15 s before being returned to its home cage. Swimming trajectories were recorded using a computerized video-tracking system (Ethovision, Noldus, The Netherlands) logging path length, escape latency and swim speed. Four days after finishing the acquisition phase, a probe trial was performed. The platform was removed from the maze, and each mouse was allowed to swim freely for 100 s. Spatial accuracy was expressed as the percentage of time spent in each quadrant of the MWM, and the number of crossings through the target position, i.e. the specific location of the platform during the acquisition phase. Statistics for behavioural analysis: Two-way repeated measures analysis of variance (RM-ANOVA), with treatment and trial block as possible sources of variation, combined with Tukey's HSD post hoc procedure, assessed the significance of differences between mean scores during the acquisition phase. Spatial acuity during the probe trial was probed using two-way ANOVA with Tukey's HSD test. Two-tailed Student's t-test (t-test) was used to evaluate differences in the number of entries through the previous target position and path length during probe trial. All statistics were performed using Sigmastat software (SPSS Inc., Erkrath, Germany) with the level of probability set at 95%.

Immunohistochemistry and Microscopy Analyses

Anesthetized animals were transcardially infused with PBS. For biochemical analyses, left cortex and hippocampus were dissected, weighted and nitrogen frozen. The right hemi-brain was post-fixed in 4% paraformaldehyde in PBS for 24 hours and paraffin embedded. Five-micrometer sections were sequentially (a) deparaffined in xylene, (b) rehydrated in ethanol, (c) permeabilized in PBS 0.05% saponine, (d) blocked in PBS 0.01% saponine, 5% normal goat serum and (d) incubated over-night with the primary antibody. For amyloid plaques labelling of amyloid plaques with the mouse monoclonal 4G8 antibody, a treatment with 80% formic acid for 30 minutes was performed. A step of antigen retrieval in citric acid (0.1M)/sodium citrate (0.1M) buffer was necessary for several antibodies. Secondary antibodies were applied one hour at room temperature. All the antibodies are listed in supplementary table 1. Images were taken with a Nikon microscope (Eclipse 800) and a digital QIMAGING camera (CCD QICAM cooled plus RGB filter pixel 4.65×4.65 µm). Control and test slices were processed the same day and under the same condition Stereological analyses were performed on 3 section levels per mouse, with 3-5 contiguous slices per level. To determine the surface and number of amyloid deposits in anatomic region of interest, the Histolab® image analyzer software (Microvision Instruments, Paris, France) was set up to automatically detect in a blind fahsion DAB labeled deposits. Plaques for which the intensity was not sufficient above the background for proper thresholding were not considered. The parameters setting remained unchanged for all analyses. Each DAB positive object was considered as an amyloid plaque and the image analyzer directly measured its surface or number. For each slice, the amyloid deposits quantification was then reported to the surface of the cortex and hippocampus of the same slice. The count of GFAP and Iba-1 positive cells was performed according to the same procedure.

Statistical Analyses

All statistical procedures, except for behavioural analyses, were performed using StatView 5.0 and JMP 7.0 softwares for Macintosh. In vitro data were analyzed by ANOVA followed by Student's t-test post hoc multiple comparison when appropriate. Because of small animal groups, data from in vivo experiments were analyzed using the non-parametric Mann-Whitney U-test. Error of the mean values in the text and bars on graphs stand for standard-error-of-the-mean (S.E.M.).

Results

CYP46A1 Gene Expression is Markedly Down-Regulated in a Murine Neuronal Cell Line Producing Aβ40 and 42 Peptides.

Figure 1A:
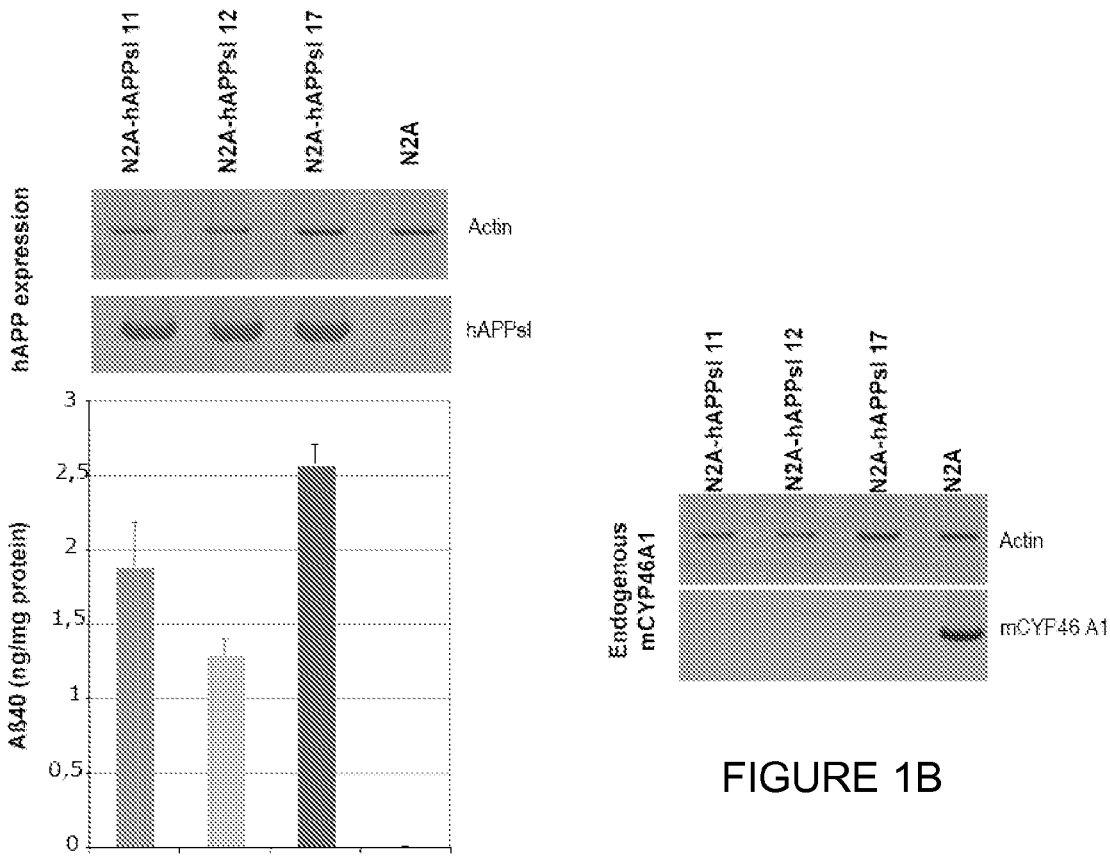

The inventors designed murine neuroblastoid N2A-cell lines (thereafter referred to as N2A-hAPPsI) that constitutively overexpress the human mutated APP gene harboring the Swedish and London mutations and secretes Aβ40 and 42 peptides (FIG. 1A).

The N2A-hAPPsI cell line responded to different hypocholesterolemiant treatments (methyl β-cyclodextrine, lipoprotein deficient serum medium) resulting in a decrease of Aβ40 and 42 peptide secretion.

Figure 1B:
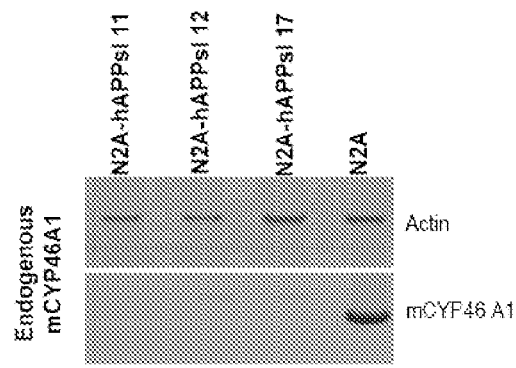

As seen by RT-PCR, the expression of murine CYP46A1 gene is markedly decreased in N2A-hAPPsI (FIG. 1B), whereas the expression of other genes involved in cholesterol metabolism remain unchanged. Theses results were confirmed by quantitative RT-PCR studies.

Figure 1C:
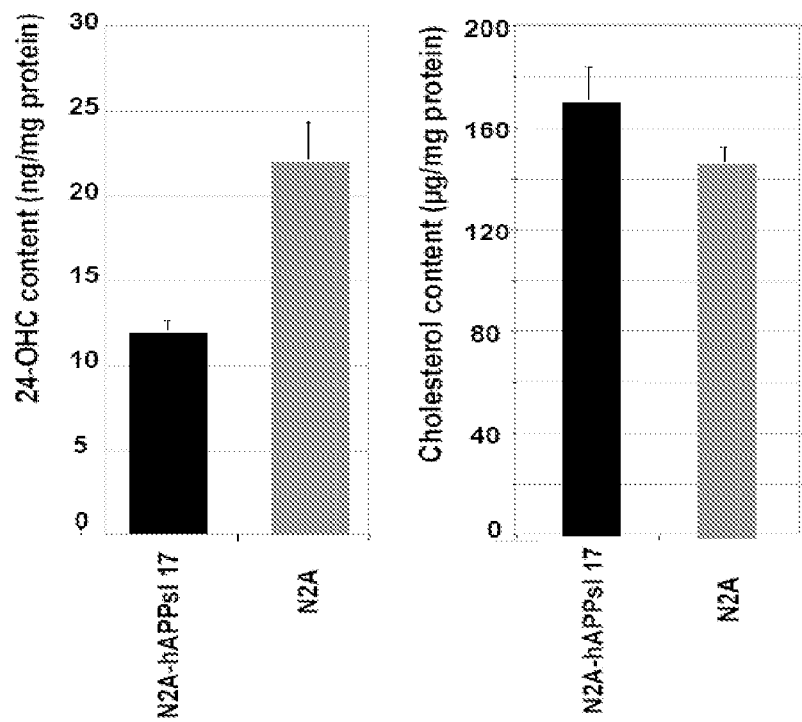

In agreement with the down-regulation of CYP46A1 gene, the level of 24-hydroxycholesterol is markedly reduced in the N2A-hAPPsI cell line, whereas the intracellular content of cholesterol is unchanged (FIG. 1C).

Re-Expression of CYP46A1 Gene in Murine Neuronal Cell Line Expressing Mutant Form of APP Results in Decreased Secretion of Aβ40 and Aβ42 Peptides in a Gene-Dose-Dependant Manner.

Figure 2A:
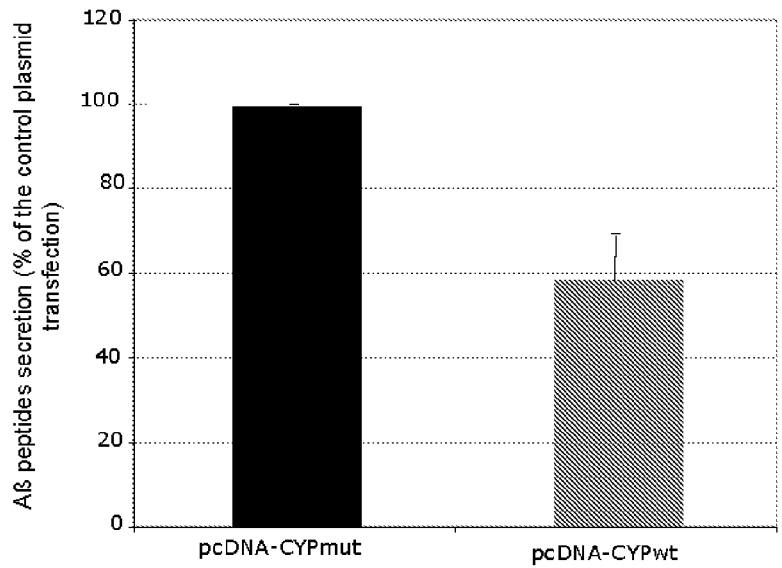

Transfection of N2A-hAPPsI cell line with a pcDNA plasmid encoding the human CYP46A1 cDNA resulted in the decreased secretion of Aβ40 et 42 peptides (FIG. 2A). The inventors then designed three N2A-hAPPsI cell lines that constitutively express the human CYP46A1 gene (thereafter referred as N2A-hAPPsI-CYP-A, B and C). Forced expression of CYP46A1 gene resulted in an increase of intracellular levels of 24-hydroxycholesterol without changes in intracellular cholesterol (FIGS. 2C and D).

Figure 2B:
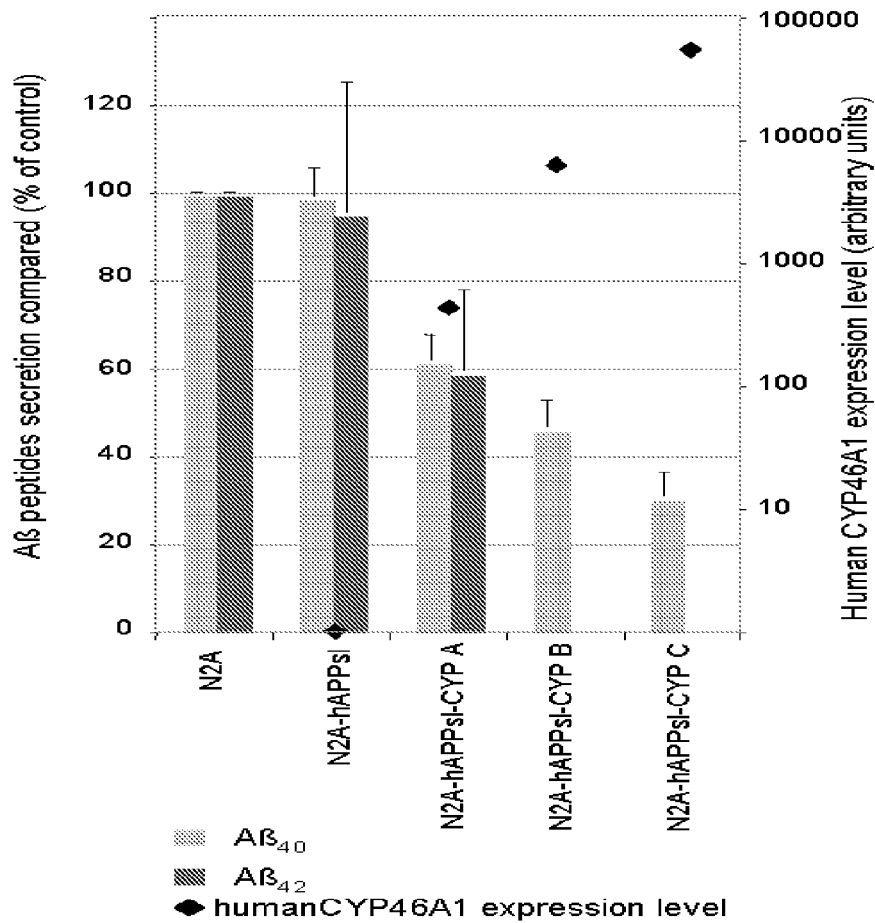

The expression of CYP46A1 gene was associated with a decreased secretion of Aβ40 et 42 peptides which correlates with the levels of CYP46A1 gene expression (FIG. 2B).

The initial cleavage of APP that generates C-terminal fragments (CTFs) and Aβ peptides is produced by aspartyl protease β-secretase, also known as β-site APP-cleaving enzyme (BACE). To determine if the decreased secretion of Aβ40 and 42 peptides in N2A-hAPPsI-CYP cell line was associated with modification of BACE clustering in the lipid rafts, the inventors evaluated the levels of BACE1 protein in detergent-resistant membrane (DRM) fractions that are enriched in cholesterol. No changes in the amount of BACE were found in the DRM fractions in which anti-flotillin protein was present.

AAV-CYP46A1 Delivery Reduces Alzheimer-Like Pathology in Transgenic APP Mice.

The APP23 (Thy1-hAPP751sI termed thereafter APP mouse) mouse develops at 6 months plaques that resemble the senile plaque in human AD (Sturchler-Pierrat, et al, 2000) and develop from the age of 3 months cognitive decline that precedes amyloid deposition (Van Dam et al, 2003).

Wild type (wt) and mutated (mt) forms of the human CYP46 cDNA tagged with HA epitope were cloned in adeno-associated-virus plasmids to generate AAV5/PGK-hCYP46A1 (referred to as AAV5-CYPwt [wildtype]) and AAV5/PGK-hCYP46A1 mut (referred to as AAV5-CYPmt [mutant forms]) vectors ($6 \times 10^{12}$ vp/ml)). The mutated form of human CYP46 contains a missense mutation destroying its heme structure leading to complete absence of 24-hydroxylase activity. The functionality of AAV plasmids was checked by transient transfection of 293T cells). AAV5-CYPwt and AAV5-CYPmt vectors were injected in the hippocampus and cerebral cortex of one and a half month old APP mice, which do not yet exhibit cognitive deficits and amyloid plaques.

Immunohistochemistry using an antibody against HA demonstrated the neuronal expression of CYP-wt and CYP-mt in neocortex and hippocampus of 6-month old treated mice. In the hippocampus, the highest expression of CYPwt or CYPmt was detected throughout the dentate gyrus, CA2 and CA3. CYP-wt and CYP-mt proteins were mostly expressed in NeuN-positive neurons and co-localize, as expected, with GRP 78 BiP protein which is expressed in endoplasmic reticulum.

Compared with untreated APP23 mice or APP23 mice treated with AAV5-CYPmt vector, the APP23 mice treated with AAV5-CYPwt vector showed increased levels of 24-hydroxycholesterol in hippocampus and neocortex (FIG. 3).

To investigate the effects of overexpressing CYP46A1 expression with AAV5-CYPwt vector on APP processing and amyloid pathogenesis in the APP23 transgenic mice, the inventors used immunohistochemical analysis for Aβ (FIGS. 4A and 4B). Compared with APP transgenic mice treated with AAV-CYPmt, 6-month old mice treated with AAV-CYPwt showed a significant reduction (55% percent reduction, n=6 in each group, p<0.05) in the percentage of area occupied by Aβ-immunoreactive plaques in the hippocampus and neocortex (injections sites) but not in other brain regions such as the thalamus where no AAV vectors were delivered.

To determine if the neuroprotective effects of AAV-CYPwt were associated with amelioration of the cognitive and performance deficits in APP transgenic mice, animal were tested in the hidden-platform Morris-water maze test to explore spatial learning and memory deficits, a finding that is reminiscent of disturbances in AD patients. Compared with APP transgenic mice treated with AAV-CYPmt, mice treated with AAV-CYPwt showed a significant improvement in the acquisition phase (path length and escape latency (FIG. 5A), swim speed (FIG. 5B) and probe trial (FIG. 5C).

Decreased Amyloid Deposition and Aβ Peptides Production in APP23 Mice Injected with AAV5-CYP46A1 Vector AAV vectors expressing wild-type (AAV5-wtCYP46A1, n=11 females) or mutated (AAV5-mtCYP46A1, n=11 females) CYP46A1 cDNA tagged with the hemaglutinin (HA) epitope were injected in hippocampus, frontal and parietal cortex of both hemispheres of 2-month-old APP23 mice. The mutant CYP46A1 protein contains a mutation that results in the complete lack of cholesterol 24-hydroxylase activity.

At age 6 (n=12) and 12 months (n=10), wild-type (wt) or mutant (mt) CYP46A1 proteins showed comparable expression in neurons from the cerebral cortex and hippocampus (FIG. 6A) where they co-localized with the GRP78 Bip marker in the endoplasmic reticulum, as did the endogenous cholesterol-24-hydroxylase (Ramirez et al, 2008) (FIG. 6B). With quantitative RT-PCR, the level of CYP46A1 mRNA was found to be eight-fold higher than the level of mouse Cyp46a1 in non-injected APP23 mouse. 24S-hydroxycholesterol increased two-fold in the dissected cerebral cortex and hippocampus of mice injected with AAV5-wtCYP46A1 vector, while total cholesterol remained unchanged (FIG. 6C).

Figure 7E:
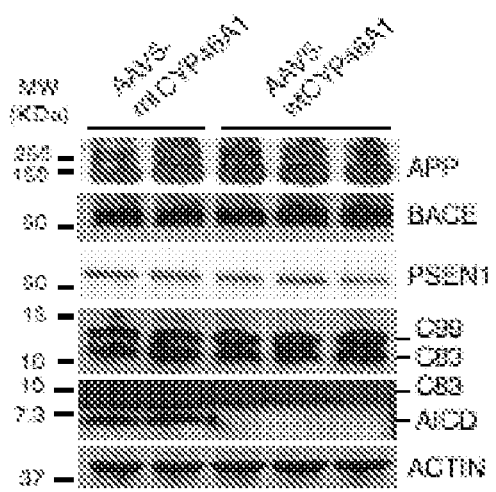
Figure 7F:
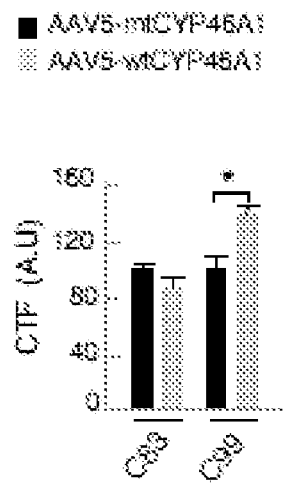
Figure 7G:
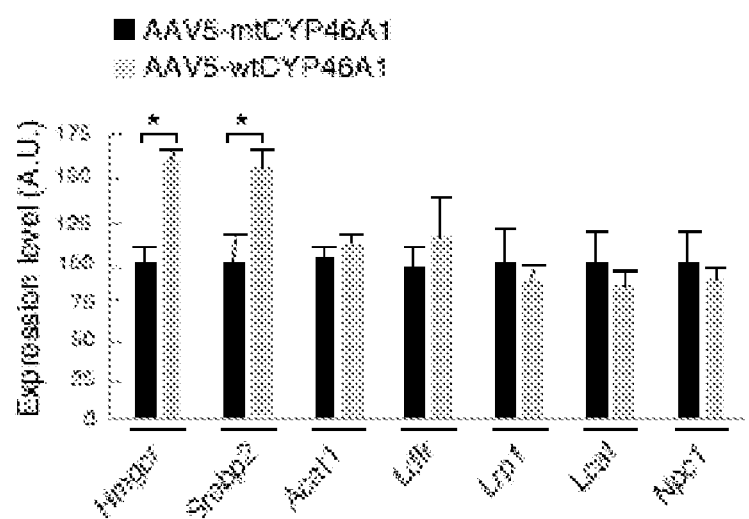

The expression of CYP46A1 gene was associated with a marked reduction in the number of amyloid plaques (63 to 68%) and percentage of area occupied by amyloid deposits (71%) in the hippocampus and cerebral cortex (FIG. 7A, B). Most remaining amyloid deposits were concentrated in regions where very few or no cells expressed the wtCYP46A1 protein. Aβ$_{40}$ and Aβ$_{42}$ peptides assessed by ELISA decreased by 50±3% and 57±4%, respectively, in pooled cerebral cortex and hippocampus samples (FIG. 7C). The amount of hexameric and dodecameric Aβ oligomers were slightly reduced without reaching statistical significance. In contrast, trimeric Aβ oligomers were decreased by 30 to 50% (P<0.05, FIG. 7D). Western blotting analysis showed that the amount of a-secretase cleavage product C83 remained unchanged whereas the l3-secretase cleavage product C99 increased by 40% in AAV5-wtCYP46A1 injected mice (FIG. 7E, F). AICD fragments generated by γ-cleavage were barely detectable (FIG. 7E), suggesting that CYP46A1 expression induced decreased cleavage of CTFs by γ-secretase in vivo.

The expression of Adam9, 10, 17, Bace1 and Psen1 and more surprisingly of LXR target genes (Abca1, Abca2, Abcg1, Abcg4, Abcg5 and ApoE) was not modified. The expression of 3-hydroxy-3-methylglutaryl-Coenzyme A reductase (Hmgcr) and sterol-binding protein 2 (Srebp2) gene was increased by 1.6 fold (FIG. 7G) without change in acyl-coenzyme A: cholesterol acyltransferase 1 (Acat1), low density lipoprotein receptor (Ldlr), low density lipoprotein-related protein 1 (Lrp1), lecithin:cholesterol acyltransferase (Lcat) and Niemann-Pick disease Cl (Npc1) gene expression.

Figure 8:
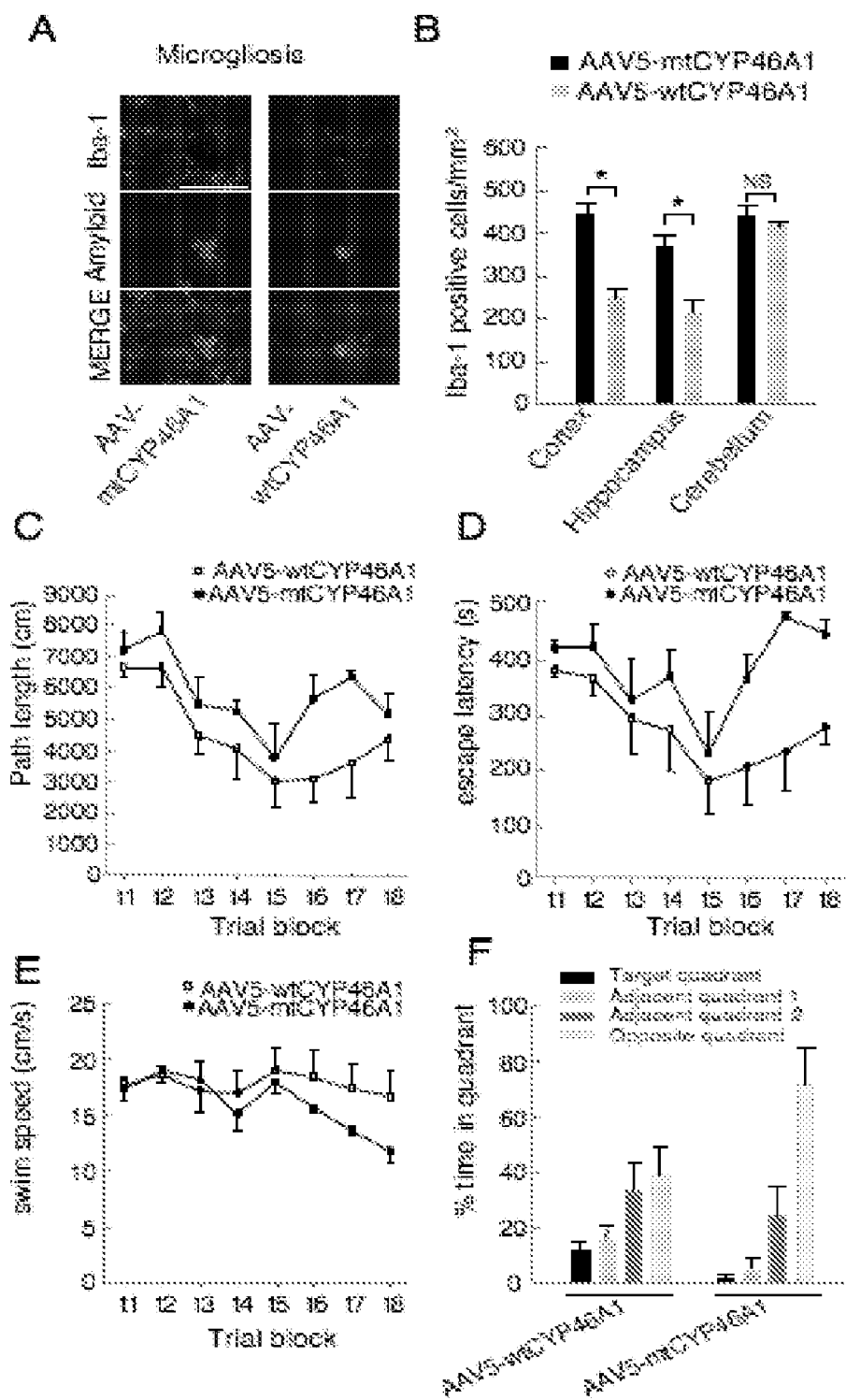

Expression of CYP46A1 Decreases Microgliosis and Improves Cognitive Deficits Before the Onset of Amyloid Deposits Amyloid deposits induce a microglial response and astrocytosis in APP23 mice (Bornemann et al, 2001). The number of microglial Iba-1 positive cells was reduced by 41±7 and 46±4% respectively in the cerebral cortex and hippocampus injected with AAV5-wtCYP46A1 vector (FIG. 8A, B). Similarly, the number of GFAP-positive cells was reduced by almost 50% in APP23 mice injected with AAV5-wtCYP46A1 vector.

APP23 mice develop moderate cognitive deficits at 3 months old, while amyloid deposits are only detected in their brain at 6 months (Van Dam, 2003). To evaluate the effects of AAV5-wtCYP46A1 vector injection on cognitive functions, mice were tested at 6 months using the Morris water maze (MWM) procedure. All mice injected with either AAV5-wtCYP46A1 or AAV5-mtCYP46A1 vectors showed improved performances during the acquisition phase (P<0.001) (FIG. 8C, D). The inventors observed however a significant effect of AAV5-wtCYP46A1 injection on path length parameter (P=0.054, two-way RM-ANOVA) with no significant interaction between vector injection and trial block (P=0.583) (FIG. 8C). The absence of treatment effects on swim speed (FIG. 8E) indicated that the improvement in path length was not due to a better motor performance. The inventors observed no significant effect of vector injection on escape latency (FIG. 8D). During the probe trial, mice injected with AAV5-wtCYP46A1 vector did not spend more time in the target quadrant (FIG. 8F) but they crossed more frequently (1.4±0.4) the previous platform position than sham-treated APP23 mice (0±0, P=0.018) indicating that their spatial memory was improved.

Figure 9:
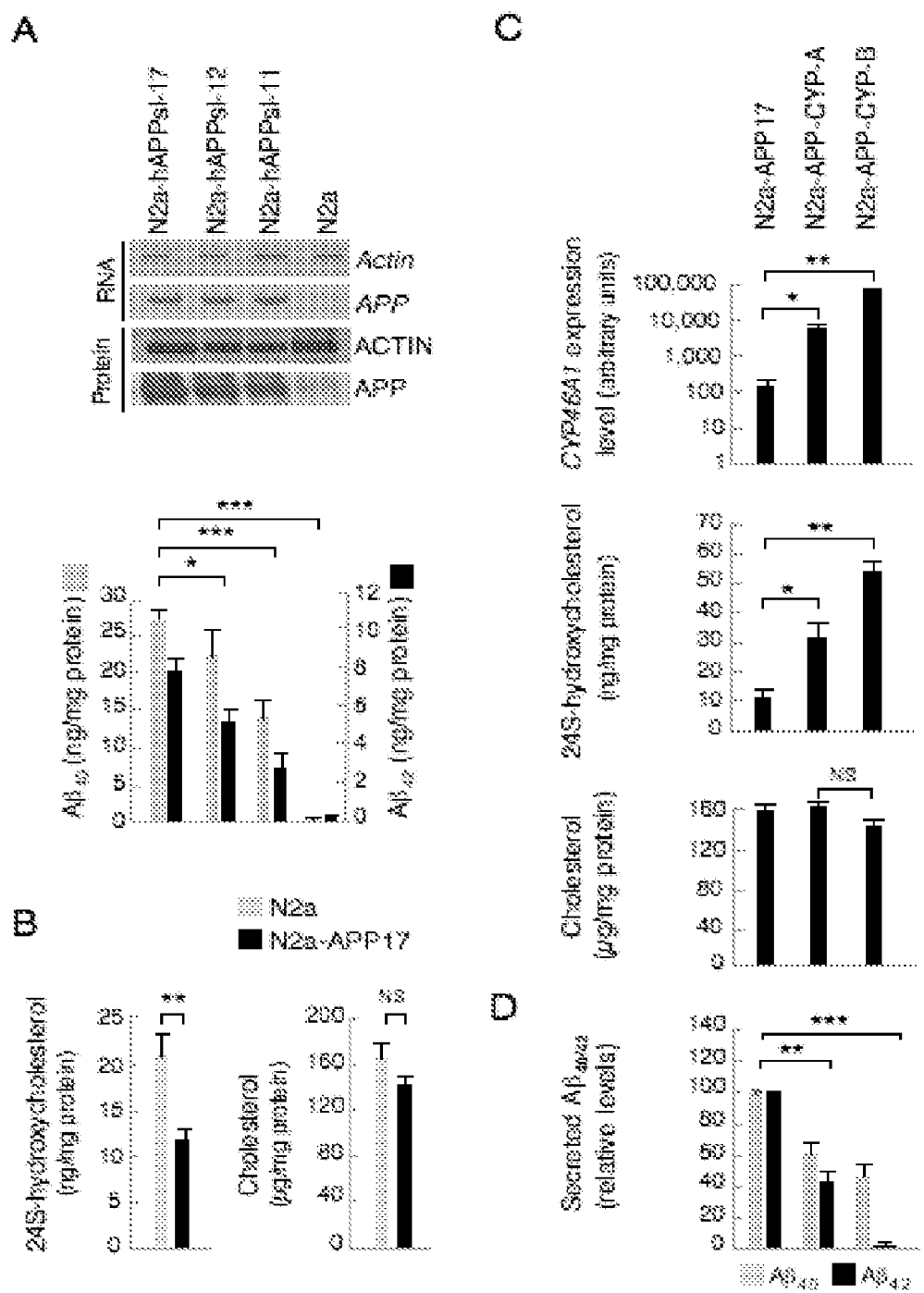

Expression of CYP46A1 Decreases the Amount of Cholesterol and Presenilin-1 in Detergent-Resistant Membranes Isolated from Murine Neuroblastoid Cells Expressing Mutated Human APP To get more insight on the mechanisms by which CYP46A1 overexpression reduces AICD fragments generated by γ-cleavage in vivo, the inventors engineered murine neuroblastoid N2a cell lines to constitutively overexpress the human APP gene harboring the Swedish and London mutations (APPsl). The inventors selected clone 17 (herein after called N2a-APP17) that was found to secrete the highest levels of Aβ$_{40/42}$ peptides (FIG. 9A) and demonstrated that this clone had a decreased expression of murine Cyp46a1 gene and a 43% reduction of 24S-hydroxycholesterol content (FIG. 9B).

The inventors then restored the expression of cholesterol-24-hydroxylase by engineering N2a-APP17 cells to overexpress the human CYP46A1 gene. They obtained two cell lines, called N2a-APP-CYP-A and -B, that showed an increase of 24S-hydroxycholesterol with no significant change in total cholesterol level (FIG. 9C). In these cells, a decrease of Aβ40 and Aβ42 peptide secretion was observed, which was inversely proportional to the increased 24S-hydroxycholesterol content ($r^2$=0.91) (FIG. 9D). Aβ42 peptides were barely detectable in the cells that expressed the highest level of CYP46A1 gene. This effect was not due to modifications of the expression of APPsl transgene nor of murine Adam9, Adam10, Adam17, Bace1 and Presenilin1 (Psen1) involved in APP processing, nor of 3-hydroxy-3-methylglutaryl-Coenzyme A reductase (Hmgcr), the rate limiting enzyme of cholesterol synthesis, and nor of ATP binding cassette transporter A1 (Abca1) and Apolipoprotein E (ApoE).

To characterize APP processing by secretases in N2a-APP-CYP cells, the inventors quantified the C-terminal fragments (CTF) of APP by western blotting in crude cell extracts. The α-secretase cleavage product C83 content was not modified in N2a-APP-CYP-A and -B cells. The β-secretase cleavage product C99 peptide increased by 37% in N2a-APP-CYP-A cells and reduced by 34% in N2a-APP-CYP-B cells. The γ-secretase cleavage product AICD was lowered by 50 to 65% in both N2a-APP-CYP-A and -B cells (FIG. 10A). The concomitant decrease of AICD and increase of β-CTF in N2a-APP-CYP-A cells are consistent with the fact that CYP46A1 overexpression acts mostly at the level of CTF cleavage by γ-secretase. At highest level of expression, CYP46A1 also seems to decrease β-CTF without change in the amount of BACE1 in DRM, suggesting an additional effect on β-secretase activity.

Mounting evidence argues that lipid rafts, biochemically defined as detergent-resistant membranes (DRM), are the principal membrane microdomains in which the amyloidogenic processing of APP occurs (Cordy et al, 2006). Lipid rafts are enriched in cholesterol and γ-secretase complex co-resides with APP and β-secretase in these microdomains (Li et al, 2000; Wahrle et al, 2002; Vetrivel et al, 2004). Changes in content of cholesterol in lipid rafts can markedly influence the production of Aβ (Ehehalt et al, 2003; Won et al, 2008).

In N2a-APP17 cells overexpressing the CYP46A1 gene, the amount of cholesterol was decreased by 28% and 45% in the two flotillin-2 positive DRM fractions of N2a-APP-CYP-A and -B cells respectively (FIG. 10B). APP resides both in raft and non-raft domains and the percentage of APP localized in the two flotillin-2 positive DRM fractions of N2a-APP17 cells represented 40% of the total amount of APP (FIG. 10C). In the same enriched cholesterol fractions from N2a-APP-CYP-A and -B cells, the amount of BACE1 was not modified but APP was reduced by 32 and 45% and PSEN1, a component of γ-secretase, was lowered by 25 and 67% respectively (FIG. 10C). Altogether, these results suggest that the decreased cleavage of CTF by γ-secretase in N2a-APP17 cells overexpressing CYP46A1 results from a reduction of cholesterol in DRMs that was associated with a decreased recruitment or stabilization of APP and PSEN1 in the same microdomains.

REFERENCES

Berns, K I "Parvoviridae and their Replication" in Fundamental Virology, 2nd Edition, (B. N. Fields and D. M. Knipe, eds.
Bieche, I. et al. Clin Cancer Res, 10, 6789-95 (2004).
Bornemann, K. D., et al. Am J Pathol, 158, 63-73 (2001).
Brown, J., 3rd et al. J Biol Chem 279, 34674-81 (2004).
Capecchi, M. R., Cell, 22: 479-488, (1980).
Carter, B. J., Current Opinion in Biotechnology, 3: 533-539, (1992).
Cordy, J. M., et al. Mol Membr Biol, 23, 111-22 (2006).
Chu et al., Gene, 13: 197, (1981).
Cutler, R. G. et al. Proc Natl Acad Sci USA 101, 2070-5 (2004).
Davidson et al., PNAS USA, 97 (7): 3428-3432 (2000).
Davis et al. (1986) Basic Methods in Molecular Biology, Elsevier.
Dietschy, J. M. & Turley, S. D. J Lipid Res 45, 1375-97 (2004).
Edge, Nature, 292: 756, (1981).
Ehehalt, R., et al, J Cell Biol, 160, 113-23, (2003).
Feigner et al., Proc. Natl. Acad. Sci., USA, 84: 7413-7417, (1987).
Graham et al., Virology, 2: 456-467, (1973).
Grimm, M. O. et al. Nat Cell Biol 7, 1118-23 (2005).
Hutter-Paier, B. et al. Neuron 44, 227-38 (2004).
Jay et al., J. Biol. Chem., 259: 6311, (1984).
Jin, L. W., et al. Am J Pathol 164, 975-85 (2004).
Kivipelto, M. et al. Ann Intern Med 137, 149-55 (2002).
Klein et al., Nature, 327: 70-73, (1987).
Kolsch, H. et al. Neurosci Lett 368, 303-8 (2004).
Kotin, R. M., Human Gene Therapy, 5: 793-801 (1994).
Lebkowski et al., Molec. Cell. Biol. 8: 3988-3996, (1988).
Li, Y. M., et al. Nature, 405, 689-94 (2000).
Mannino et al., BioTechniques, 6: 682 690, (1988).
Mori, T. et al. J Neuropathol Exp Neurol 60, 778-785. (2001).
Muzyczka, N., Current Topics in Microbiol. And Immunol., 158: 97-129, (1992).
Namba, Y., et al, Brain Res 541, 163-166, (1991).
Nambair et al., Science, 223: 1299, (1984).
Ohyama, Y., et al. J Biol Chem 281, 3810-3820 (2006)
Ramirez, D. M., et al. J Comp Neurol, 507, 1676-93 (2008).
Refolo, L. M. et al. Neurobiol Dis 8, 890-9. (2001).
Shelling and Smith, Gene Therapy: 165-169, (1994).
Shigekawa et al., BioTechniques, 6: 742-751, (1988).
Sambrook et al. (1989) Molecular Cloning, a laboratory manual, Cold Spring Harbor Laboratories, New York.
Sevin, C., et al. Hum Mol Genet, 15, 53-64 (2006).
Simons, M. et al. Proc Natl Acad Sci USA 95, 6460-6464 (1998).
Strittmatter, W. J. et al. Proc Natl Acad Sci USA 90, 1977-1981 (1993).
Sturchler-Pierrat, C., et al. Proc Natl Acad Sci USA, 94, 13287-92 (1997).
Sturchler-Pierrat, CC & Staufenbiel, M. Ann N Y Acad Sci, 920, 134-9 (2000).
Van Dam, D. et al, Eur J Neurosci, 17, 388-96 (2003).
Vetrivel, K. S. et al. J Biol Chem, 279, 44945-54 (2004).
Vetrivel, K. S. et al. J Biol Chem 280, 25892-900 (2005).
Vincent et al., Vaccines 90 (Cold Spring Harbor Laboratory Press), 1990.
Wahrle, S., et al. Neurobiol Dis, 9, 11-23 (2002).
Won, J. S., et al. J Neurochem, 105, 1536-49 (2008).
Zhou et al., J. Exp. Med. 179: 1867-1875, (1994).

The invention claimed is:

1. A method for treating a subject having Alzheimer's disease, said method comprising the steps of:
   (a) providing a viral vector comprising a cholesterol 24-hydroxylase encoding nucleic acid; and
   (b) delivering the viral vector to the central nervous system (CNS) of the subject, whereby said vector transduces cells in the CNS, and whereby cholesterol 24-hydroxylase is expressed by the transduced cells at a therapeutically effective level, wherein expression of the cholesterol 24-hydroxylase gene results in a reduction in amyloid plaques in the treated subject having Alzheimer's disease as compared to a non-treated subject having Alzheimer's disease.

2. The method according to claim 1, wherein said viral vector comprises a nucleic acid sequence that encodes an amino acid sequence of SEQ ID NO: 2.

3. The method according to claim 2, wherein said viral vector comprises a sequence of SEQ ID NO: 1.

4. The method according to claim 1, wherein said viral vector is selected from the group consisting of adenovirus, retrovirus, herpesvirus and Adeno-Associated Virus (AAV) vectors.

5. The method according to claim 4, wherein said viral vector is an AAV vector.

6. The method according to claim 4, wherein said viral vector is an AAV5, AAV6, AAV9 or AAV10 vector.

7. The method according to claim 4, wherein said viral vector is a pseudotyped AAV vector.

8. The method according to claim 1, wherein the vector is delivered directly into the brain of the subject.

9. The method according to claim 8, wherein the vector is delivered to the ruber nucleus, corpus amygdaloideum, entorhinal cortex, temporal lobe of the cortex, cerebral cortex, neurons in ventralis lateralis, or the anterior nuclei of the thalamus, by stereotaxic microinjection.

10. The method according to claim 1, wherein the vector is delivered by intravascular or intrathecal injection, or by injection into the cerebrospinal fluid.

11. The method according to claim 10, wherein the vector is delivered by intravenous or intra-arterial injection.

12. The method according to claim 10, wherein the vector is delivered by intrathecal injection.

13. The method according to claim 10, wherein the vector is delivered by injection into the cerebrospinal fluid.

* * * * *